United States Patent [19]

Ohnmacht, Jr., et al.

[11] Patent Number: 5,455,253

[45] Date of Patent: Oct. 3, 1995

[54] HETEROCYCLIC DERIVATIVES

[75] Inventors: Cyrus J. Ohnmacht, Jr.; Diane Trainor; Janet M. Forst; Mark M. Stein; Robert J. Harris, all of Wilmington, Del.

[73] Assignee: Zeneca Limited, United Kingdom

[21] Appl. No.: 227,833

[22] Filed: Apr. 14, 1994

Related U.S. Application Data

[63] Continuation-in-part of Ser. No. 135,896, Oct. 13, 1993, abandoned.

[30] Foreign Application Priority Data

Oct. 20, 1992 [GB] United Kingdom ............... 9221989
Apr. 20, 1993 [GB] United Kingdom ............... 9308065

[51] Int. Cl.$^6$ ............... C07D 215/20; C07D 405/04; A61K 31/435
[52] U.S. Cl. ............... 514/311; 514/297; 514/314; 546/102; 546/104; 546/167; 546/168; 546/173
[58] Field of Search ............... 546/167, 168, 546/102, 104, 173; 514/314, 311, 297

[56] References Cited

U.S. PATENT DOCUMENTS

| | | | |
|---|---|---|---|
| 3,857,849 | 12/1974 | Meyer et al. | 260/295.5 R |
| 3,867,393 | 2/1975 | Meyer et al. | 260/294.8 F |
| 3,935,223 | 1/1976 | Meyer et al. | 260/295.5 R |
| 3,946,026 | 3/1976 | Meyer et al. | 260/295.5 A |
| 4,022,898 | 5/1977 | Meyer et al. | 424/251 |
| 4,546,186 | 10/1985 | Abou-Gharbia | 546/167 |
| 4,723,014 | 2/1988 | Anderson et al. | 546/286 |
| 4,732,898 | 3/1988 | Badger et al. | 514/225 |
| 4,769,375 | 9/1988 | Meyer et al. | 514/311 |
| 4,820,842 | 4/1989 | Anderson et al. | 546/135 |
| 4,895,855 | 1/1990 | Goldmann et al. | 514/302 |

FOREIGN PATENT DOCUMENTS

| | | | |
|---|---|---|---|
| 0197488 | 10/1986 | European Pat. Off. | 514/311 |
| 0299727 | 1/1989 | European Pat. Off. | 514/311 |
| 0539154 | 4/1993 | European Pat. Off. | 514/311 |
| 0539153 | 4/1993 | European Pat. Off. | 514/311 |
| 0567107 | 10/1993 | European Pat. Off. | 514/311 |
| 2003148 | 7/1971 | Germany | 514/311 |
| 2018738 | 10/1971 | Germany | 514/311 |
| 2718130 | 9/1978 | Germany | 514/311 |
| 1575281 | 9/1980 | United Kingdom | 514/311 |
| WO9012015 | 10/1990 | WIPO | 514/311 |
| WO9115485 | 10/1991 | WIPO | 514/311 |
| WO9115484 | 10/1991 | WIPO | 514/311 |

OTHER PUBLICATIONS

Chemical Abstracts, vol. No. 11, Abstract 97424d, p. 690, Sep. 10, 1990, Lielbriedis et al.

Rose, *Arzheim–Forsch*, 39 (11), pp. 1393–1398, Nov. 1989.

Chemical Abstracts, vol. 75, No. 13, Abstract 98.459C, p. 307, Sep. 27, 1971.

P. Cupka, et al. "Synthesis and Spectral Properties of Substituted 1,4–Dihydropyridines and 1,4,5,6,7, 8–Hexahydroquinolines" *Collect Czech. Chem. Comm.*, (1978), 52(3), 742–751.

E. Grinshteins et al. *Khim. Geterotsikl, Seodin*, (1967), 6, 1118–1120.

R. Vitolinya et al. *Khim–Farm. Zh.*, (1981), 15(1), 39–42.

A. Dreimane et al. *Khim. Gererotsikl. Soedin*, (1980), 6, 791–5.

Rose, Ulrich, "Hexahydroquinolinones with calcium–modulatory effects. Synthesis and pharmacological efficacy", *Arch. Pharm.*, (1990), 281–6.

Rose, Ulrich, "Calcium modulators of the anellated dihydropyridine type. Synthesis and pharmacological action", *Arzneim.–Forsch.*, (1989), 1393–8.

S. M. Jain, et al. "Synthesis and Pharmacological screening of 1,8–dioxo–9–(substitutedphenyl)–1,2,3,4,5,6,7,8,9, 10–decahydroacridines" *Ind. J. Chem.* (1991), 1037–1040.

H. Antaki "The Synthesis of Ethyl 4–Aryl–5,6,7, 8–tetrahydro–5–oxo–guinoline–3–carboxylates and their Derivatives" *J. Chem. Soc.* (1963), 4877–4879.

Magid Abou–Gharbia "Synthesis of Novel Hexahydroquinolines and Hexahydroacridines" *Heterocycles* (1986), 24, 1347–1353.

*Primary Examiner*—Alan L. Rotman
*Assistant Examiner*—Zinna N. Davis
*Attorney, Agent, or Firm*—Cushman Darby & Cushman

[57] ABSTRACT

Compounds of formula I

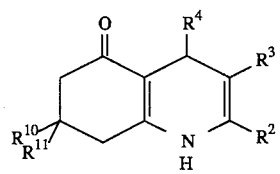

wherein $R^2$, $R^3$, $R^4$, $R^{10}$ and $R^{11}$ have any of the meanings given in the specification, and their pharmaceutically acceptable salts are useful in the treatment of urinery incontinence. Also disclosed are pharmaceutical compositions, processes for preparing the compounds of formula I and intermediates.

19 Claims, No Drawings

HETEROCYCLIC DERIVATIVES

This application is a continuation-in-part of application Ser. No. 08/135,896, filed on 13 Oct. 1993 now abandoned.

This invention relates to a novel group of compounds which are useful in the treatment of bladder instability in mammals such as man. More specifically, this invention relates to a group of 4,6,7,8-tetrahydro-5(1H)-quinolones, their use in the treatment of urinary incontinence in mammals (including man), processes for preparing them and pharmaceutical compositions containing them.

The existing treatments for urinary incontinence are generally poor, relying on drugs that had originally been developed for other indications. One group of such drugs comprises the calcium channel blockers, such as nifedipine, which were originally developed and are primarily used as cardiovascular agents.

Nifedipine belongs to a structural class of compounds known as the dihydropyridines. This structural class has been extensively investigated, and the structural requirements for calcium blocking activity are now quite well established. Thus, as described on Chapter 14.1 of the medicinal chemistry text book, Comprehensive Medicinal Chemistry, Volume 3, Edited by John C. Emmett and Published by Pergamon Press in 1990, the compounds possess a 1,4-dihydropyridine ring having, optimally, an aryl group at the 4-position and ester groups at the 3- and 5-positions. Removing the ester groups or replacing them with acetyl or cyano groups is associated with a reduction in activity. Generally, the compounds have methyl groups at the 2- and 6-positions.

Grinshteins et al, Khim. Geterotsikl. Soedin. (6), 1118–20, 1967 disclose the compounds 3-cyano-4-phenyl-2,7,7-trimethyl-4,6,7,8-tetrahydro-5(1H)-quinolone and 3-ethanoyl-4-phenyl-2,7,7-trimethyl-4,6,7,8-tetrahydro-5(1H)-quinolone. Vitolinya et al, Khim.-Farm. Zh., 15(1), 39–42, 1981 discloses an investigation of the effect of several 4,6,7,8-tetrahydro-5(1H)-quinolones having an ester or cyano group at the 3-position on the cardiovascular system and on intestinal smooth muscle. 3-Cyano-4-phenyl-2,7,7-trimethyl-4,6,7,8-tetrahydro5(1H)-quinolone is reported to possess hypotensive properties and to be capable of blocking the spasmogenic effect of both acetylcholine and barium chloride on intestinal smooth muscle.

DE 2003148 discloses a group of 1,4-dihydropyridine derivatives, including certain 4,6,7,8-tetrahydro-5(1H)-quinolones, which possess an ester or keto group at the 3-position and which are said to display a wide and multi-faceted pharmacological spectrum of action. The main effects said to be displayed by the compounds include strong muscular spasmoytic effects which become evident in the smooth musculature of the gastrointestinal tract, of the urogenital tract and of the respiratory system. Other main effects are stated to be on the heart (a "heart-relieving" effect) and in reducing the blood pressure of normotonic and hypertonic animals, so that they can be used as antihypertensive agents.

S. M. Jain et al, Indian Journal of Chemistry, Volume 30B, November, 1991, pages 1037–1040 discloses the synthesis and pharmacological screening of certain 9-(substituted phenyl)-1,8-(2H,5H)-acridinediones. The compounds were found to possess varying degrees of hypotensive, anti-inflammatory and anti-implantation activities.

It is known that bladder tissue is excitable and that urinary incontinence can be caused by uncontrolled or unstable bladder contractions. A group of compounds have been found that are unexpectedly capable of relaxing bladder smooth muscle, thus preventing or ameliorating uncontrolled or unstable bladder contractions. Hence, the compounds may be useful for the treatment of urge incontinence, which includes for example detrusor instability, which may result from cystitis, urethritis, tumors, stones, diverticuli or outflow obstruction; and detrusor hyperreflexia, which may result from stroke, dementia, parkinsons, suprasacral spinal-cord injury or suprasacral spinalcord disease. Some of the compounds have been found to possess the further unexpected property that they are capable of acting selectively on the bladder without at the same time significantly affecting the cardiovascular system, as indicated by heart rate and blood pressure measurements. Thus, these compounds may be particularly useful to treat urinary incontinence in patients, such as for example the elderly, for whom cardiovascular effects, such as a hypotensive effect, are particularly undesirable.

It has also unexpectedly been found that compounds according to the invention are potassium channel openers. It is known that by functioning to open potassium channels, potassium channel opening compounds can thereby function to relax smooth muscle. While not wishing to be bound by theory, it is accordingly believed that the compounds of this invention function by opening potassium channels in bladder cells and thereby relax bladder smooth muscle tissue, thus preventing or ameliorating uncontrolled bladder contractions which can cause urinary incontinence. Nurse D. A., Restorick J. M., and Mundy A. R., British Journal of Urology, (1991), 68, 27–31 discloses that cromakalim, which is well known as a potassium channel opener, has been found to be effective in a preliminary clinical trial for the treatment of urinary incontinence.

The structural requirements for activity in the 4,6,7,8-tetrahydro-5(1H)-quinolones according to the present invention have been found to be different from those expected of dihydropyridine calcium blockers. It is accordingly believed that the present invention is based upon the discovery of a new pharmacological class of bladder-relaxant dihydropyridines.

This invention provides a compound of formula I (formula set out, together with other formulae referred to by Roman numerals, on pages following the Examples), or a pharmaceutically acceptable salt thereof, wherein: either $R^2$ is hydrogen, (1–6C)alkyl or (1–4C)fluoroalkyl; and $R^3$ is hydrogen, cyano, (1–6C)alkyl, (1–6C)fluoroalkyl or ethanoyl; or $R^2$ and $R^3$ when taken together form a 1,4-butandiyl;

$R^4$ is 2- or 3-thienyl or furyl substituted at the 4- and/or 5-position(s) by a radical or radicals independently selected from a group (a) consisting of nitro, cyano, halo, (1–4C)alkyl, (1–4C)alkylsulphonyl and 2-thienyl provided that a 3-thienyl or furyl group may only be substituted at the 5-position; or $R^4$ is a 2-pyridyl which is substituted at the 5 position and/or either at the 4 position or the 6 position by a member of the above group (a); or $R^4$ is a 3-pyridyl which is substituted at the 6 position by a member of the above group (a); or $R^4$ is a 4-pyridyl which is substituted at the 2 position by a member of the above group (a); or $R^4$ is a group of formula II,

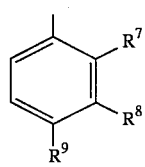

wherein:

R$^7$ is hydrogen; and

R$^8$ and R$^9$ are independently selected from hydrogen, hydroxy (1–4C)alkoxy, nitro, cyano, (1–4C)fluoroalkyl, (1–4C)fluoroalkoxy, halo, (1–4C)alkyl, (1–4C)alkanoyl, phenyl and (1–4C)alkylsulphonyl; or R$^8$ and R$^9$ taken together are (1–3C)alkylenedioxy; and R$^{10}$ and R$^{11}$ are each independently hydrogen or (1–4C)alkyl, but excluding 3-cyano-4-phenyl-2,7,7-trimethyl-4,6,7,8-tetrahydro-5(1H)-quinolone and 3-ethanoyl-4-phenyl-2,7,7-trimethyl-4,6,7,8-tetrahydro-5(1H)-quinolone.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

Particular values of 2- or 3-thienyl or furyl substituted at the 4- and/or 5-positions include 4-bromo-2-thienyl, 5-bromo-2-thienyl, 5-methylsulphonyl-2-thienyl, 5-methyl-2-thienyl, 5-(2-thienyl)-2-thienyl, 4-nitro-2-thienyl, 5-nitro-2-thienyl, 4-cyano-2-thienyl, and 5-nitro-3-thienyl.

Particular values of (1–6C)alkyl include methyl, ethyl, propyl, isopropyl, butyl, isobutyl, sec-butyl, and tert-butyl, pentyl, 3-methylbutyl, 1-ethylpropyl, hexyl, or 4-methylpentyl.

Particular values of (1–4C)alkyl include methyl, ethyl, propyl, isopropyl, butyl, isobutyl, sec-butyl, and tert-butyl.

Particular values of (1–4C)fluoroalkyl include trifluoromethyl and pentafluoroethyl.

Particular values of (1–4C)alkoxy include methoxy, ethoxy propoxy, isopropoxy, butoxy, isobutoxy, sec-butoxy, and tert-butoxy.

Particular values of (1–4C)fluoroalkoxy include trifluoromethoxy and pentafluoroethoxy.

A particular value of (1–4C)alkanoyl is ethanoyl.

A particular value of (1–4C)alkylsulphonyl is methanesulphonyl.

Particular values of (1–3C)alkylenedioxy are methylenedioxy and ethylenedioxy.

Preferred values of R$^8$ include hydrogen, hydroxy, methoxy, nitro, cyano, trifluoromethyl, trifluoromethoxy, methyl, ethyl, isopropyl and halo and ethanoyl.

Preferred values of R$^9$ include hydrogen, hydroxy, methoxy, nitro, cyano, trifluoromethyl, trifluoromethoxy, methyl, ethyl, isopropyl and halo.

Particular values for R$^2$ are methyl, ethyl, propyl, isopropyl, butyl, isobutyl, sec-butyl, tert-butyl and trifluoromethyl.

Particular values for R$^3$ are hydrogen, cyano, ethanoyl, or together with R$^2$ 1,4-butandiyl.

Compounds in which R$^3$ is hydrogen or R$^2$ and R$^3$ when taken together form a 1,4-butandiyl have been found to possess particularly good potency and selectivity for the bladder and are therefore preferred.

Compounds in which R$^2$ is trifluoromethyl have been found to possess particularly good potency, selectivity for the bladder and stability, and are therefore particularly preferred.

R$^4$ is preferably a group of formula II.

Particular values for R$^4$ are phenyl, 3-methoxyphenyl, 3-nitrophenyl, 3-cyanophenyl, 3-trifluoromethylphenyl, 3-trifluoromethyl-4-cyanophenyl, 4-trifluoromethylphenyl, 3-trifluoromethoxyphenyl, 3-fluorophenyl, 3-chlorophenyl, 3-chloro-4-fluorophenyl, 3-bromophenyl, 4-fluorophenyl, 4-chlorophenyl, 3-bromo-4-fluorophenyl, 3,4-dichlorophenyl, 4-methylphenyl, 3,4-methylenedioxyphenyl and 4-nitro-2-thienyl. Most preferably R$^4$ is 3-nitrophenyl or 3-cyanophenyl.

Preferred values for R$^{10}$ and R$^{11}$ are hydrogen and methyl.

Preferably R$^{10}$ and R$^{11}$ both represent hydrogen or both represent methyl.

A particularly preferred group of compounds of formula I is that wherein either

R$^2$ is methyl, ethyl, propyl, isopropyl, butyl, isobutyl, sec-butyl, tert-butyl or trifluoromethyl; and R$^3$ is hydrogen; or R$^2$ and R$^3$ when taken together form a 1,4-butandiyl;

R$^4$ is 3-nitrophenyl or 3-cyanophenyl; and

R$^{10}$ and R$^{11}$ are both hydrogen.

Particularly preferred compounds are 2-trifluoromethyl-4-(3-nitrophenyl)-4,6,7,8-tetrahydro-5(1 H)-quinolone and 2-trifluoromethyl-4-(3-cyanophenyl)-4,6,7,8-tetrahydro-5(1H)-quinolone. Both of these compounds have been found to possess surprisingly good potency in vitro and surprisingly good selectivity for the bladder in vivo. They have also been found to possess chemical stability superior to that of the corresponding compounds of formula I wherein R$^2$ is methyl.

Additionally, the compound described at Example 43, (−)-4-(3-cyanophenyl)-2-trifluoromethyl-4,6,7,8-tetrahydro-5(1H)-quinolone, represents a preferred embodiment of the invention.

It will be appreciated by those skilled in the art that the compounds of formula I contain an asymmetrically substituted carbon, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of urinary incontinence, it being well known in the art how to prepare optically-active forms (for example, by resolution of the racemic form by synthesis from optically-active starting materials, by chiral synthesis, or by chromatographic separation using a chiral stationary phase) and how to determine efficacy for the treatment of urinary incontinence by the standard tests described hereinafter.

A compound of formula I can be made by processes which include processes known in the chemical arts for the production of structurally analogous compounds. Such processes for the manufacture of a 4,6,7,8-tetrahydro-5(1H)-quinolones of formula I as defined above are provided as further features of the invention and are illustrated by the following procedures in which the meanings of generic radicals are as given above unless otherwise qualified. Such a process can be effected, generally, (a) for a compound of formula I wherein R$^3$ is hydrogen, by decarboxylation of a corresponding carboxylic acid of formula III in which R$^{12}$ and R$^{13}$ together represent a bond, or decarboxylation and dehydration of a carboxylic acid of formula III in which R$^{12}$ is hydrogen and R$^{13}$ is hydroxy.

(b) by reacting an unsaturated ketone of formula IV with the appropriate 1,3-cyclohexanedione and ammonia or an ammonium salt.

(c) for a compound of formula I wherein $R^2$ and $R^3$ when taken together form a 1,4-butandiyl, by reacting an acridinedione of formula VI with a reducing agent.

(d) for a compound of formula I wherein $R^2$ and $R^3$ when taken together form a 1,4-butandiyl, by reacting a ketone of formula VII with the appropriate 1,3-cyclohexanedione and ammonia or an ammonium salt.

(e) by reacting an enedione of formula XII with enamine of formula XIII in which Z is an imino group in the presence of ammonia or an ammonium salt.

(f) for a compound of formula I where $R^3$ is ethanoyl or cyano reacting a compound of formula XV in which $R^{3a}$ is ethanoyl or cyano with the appropriate 1,3-cyclohexanedione and the appropriate aldehyde of formula $R^4CHO$.

The decarboxylation described in (a) can conveniently be carried out at an elevated temperature for example in the range of from 50° to 250° C., preferably, in the range of from 190° to 220° C. without an acid catalyst and preferably, in the range of from 90° to 120° C. with an acid catalyst. The non-acid catalyzed decarboxylation can be carried out as a neat melt, or in an inert solvent of appropriate boiling point such as diphenyl ether or N-methylpyrrolidin-2-one. A preferred solvent is N-methylpyrrolidin-2-one. Suitable solvents for the acid catalyzed decarboxylation include alcohols, for example, methanol or ethanol; dimethylsulfoxide; aromatic hydrocarbons such as toluene; ethers, such as for example 1,2-dimethoxyethane or diglyme; and N-methylpyrrolidin-2-one. Concentrated sulphuric acid or p-toluenesulphonic acid may conveniently be used as an acid catalyst.

Reaction (b) can conveniently be carried out at a temperature for example in the range of from 0° to 150° C., preferably at an elevated temperature, for example in the range of from 50° to 120° C. Suitable solvents for the reaction include alcohols, for example, methanol or ethanol; dimethylsulfoxide; ethers, such as 1,2-dimethoxyethane or diglyme; and carboxylic acids, for example acetic acid. A convenient ammonium salt is for example ammonium acetate.

Reaction (c) can conveniently be carried out at a temperature for example in the range from 20° to 80° C., preferably at a temperature in the range of 50° to 80° C. Suitable solvents include alcohols, for example ethanol, pyridine and mixtures thereof. Suitable reducing agents include for example sodium borohydride.

Reaction (d) can conveniently be carried out at a temperature for example in the range of from 0° to 150° C., preferably at an elevated temperature, for example in the range of from 50° to 120° C. Suitable solvents for the reaction include alcohols, for example, methanol or ethanol; dimethylsulfoxide; ethers, such as 1,2-dimethoxyethane or diglyme; and carboxylic acids, for example acetic acid. A convenient ammonium salt is for example ammonium acetate In reaction (e), Z may be, for example, a dialkylimino group such as dimethylimino, or a cyclic imino group such as pyrrolidino or piperidino.

The enamine starting material of formula XIII may conveniently be formed in situ by reaction of the appropriate ketone of formula $R^2COCH_2R^3$ with the appropriate amine The reaction is conveniently carried out at a temperature in the range of from 20° to 80° C., preferably from 50° to 80° C. Suitable solvents include alcohols such as ethanol.

Reaction (f) is conveniently performed at a temperature in the range of from 0° to 150° C., preferably from 50° to 120° C. Suitable solvents include alcohols such as ethanol.

If not commercially available, the necessary starting materials for the processes such as those described following may be made by procedures which are selected from standard organic chemical techniques, techniques which are analogous to the synthesis of known, structurally similar compounds, or techniques which are analogous to the above described procedure or the procedures described in the examples.

An intermediate of formula III can be prepared by reacting an acetoacetic ester of formula X in which ORa is an alcohol residue such as for example 2-cyanoethoxy or ethoxy with an aldehyde of formula $R^4CHO$ and the appropriate 1,3-cyclohexanedione to give an ester of formula VIII as shown in scheme I. Hydrolysis of the ester, for example by treatment with aqueous sodium hydroxide in 1,2-dimethoxyethane yields an acid of formula III. In some cases an ester of formula VIIIa may be obtained instead of an ester of formula VIII, and this may be hydrolysed to give a compound of formula IIIa. Such a procedure is illustrated in Example 15 hereinafter.

An intermediate of formula IV may be prepared by reacting the corresponding benzaldehyde of formula $R^4CHO$ with a ketone of formula XIV. The reaction is conveniently preferred in the presence of a base, for example sodium hydroxide.

An intermediate acridinedione of formula VI can be prepared as shown in Scheme II, by reacting a corresponding aldehyde of formula $R^4CHO$, or an acetal or hemiacetal thereof, with ammonia or an ammonium salt (such as ammonium acetate) and the appropriate 1,3-cyclohexanedione. The reaction can be carried out at a temperature in the range of from 0° to 150° C., preferably at an elevated temperature, for example in the range of from 50° to 120° C. Suitable solvents for the reaction include alcohols, for example, methanol or ethanol; dimethylsulfoxide; ethers, such as 1,2-dimethoxyethane or diglyme; and carboxylic acids, for example acetic acid.

As also shown in scheme II, an intermediate acridinedione of formula VI can be prepared by reacting a compound of formula IX with an aldehyde of formula $R^4CHO$, or acetal or hemiacetal thereof or a reactive derivative thereof. The reaction can be carried out at a temperature in the range of from 0° to 150° C., preferably at an elevated temperature, for example in the range of from 50° to 120° C. Suitable solvents for the reaction include alcohols, for example, methanol or ethanol; dimethylsulfoxide; ethers, such as 1,2-dimethoxy ethane or diglyme; and carboxylic acids, for example acetic acid.

An intermediate of formula VII can be prepared by condensation of 1-morpholinocyclohexene and an aldehyde of formula $R^4CHO$ followed by hydrolysis as shown in Scheme III.

An intermediate of formula XII can be prepared by reacting an aldehyde of the formula $R^4CHO$ with the appropriate 1,3-cyclohexanedione. The reaction is conveniently effected at a temperature in the range of from 0° to 80° C., preferably 40° to 80° C. Suitable solvents for the reaction include alcohols, such as ethanol.

Pharmaceutically acceptable salts may be obtained using standard procedures well known in the art, for example by reacting a compound of formula I with a suitable acid or base affording a physiologically acceptable counterion.

When used to treat urinary incontinence, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a feature of the invention.

According to another aspect, therefore, the invention provides a pharmaceutical composition, which comprises a compound of formula I or a pharmaceutically acceptable salt thereof, as defined hereinabove, and a pharmaceutically acceptable diluent or carrier.

The compositions may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular, subcutaneous or intramuscular injection or infusion; or in the form of a patch for transdermal administration.

The invention further provides a method for the treatment of urinary incontinence, comprising administering to a mammal in need of such treatment an effective amount of a compound of formula I as defined above or a pharmaceutically acceptable salt thereof.

Treatment using a compound according to the invention can be remedial or therapeutic as by administering a compound following the onset or development of urinary incontinence in a patient. Treatment can also be prophylactic or prospective by administering a compound in anticipation that urinary incontinence may develop, for example in a patient who has suffered from incontinence in the past.

According to a further aspect, the invention provides the use of a compound of formula I, as defined hereinabove, in the manufacture of a medicament for the treatment of urinary incontinence.

Because compounds according to the invention function to open cell potassium channels, they may also be useful as therapeutic agents in the treatment of other conditions or diseases in which the action of a therapeutic agent which opens potassium channels is desired or is known to provide amelioration. Such conditions or diseases include hypertension, asthma, peripheral vascular disease, right heart failure, congestive heart failure, angina, ischemic heart disease, cerebrovascular disease, glaucoma, renal cholic, disorders associated with kidney stones, irritable bowel syndrome, male pattern baldness, premature labor, and peptic ulcers.

The dose of compound of formula I which is administered will necessarily be varied according to principles well known in the art taking account of the route of administration, the severity of the incontinence condition, and the size and age of the patient. In general, a compound of formula I will be administered to a warm blooded animal (such as man) so that an effective dose is received, generally a daily dose of above 0.005, for example in the range of about 0.01 to about 10 mg/kg body weight. Preferably the compound is administered orally in this dose range.

It will be apparent to those skilled in the art that a compound of formula I can be co-administered with other therapeutic or prophylactic agents and/or medicaments that are not medically incompatible therewith. Compounds within the scope of the invention have not been found show any indication of untoward side-effects in laboratory test animals at several multiples of the minimum effective dose.

The actions of compounds of formula I as smooth muscle relaxants useful as therapeutic agents for the treatment of urinary incontinence through their action to open potassium channels and hyperpolarize the membrane potential in the bladder detrusor smooth muscle can be shown using suitably designed in vitro tests, such as the one described following. Compounds according to the invention have been found to be active at 30 μM (micromolar) or less in this test. Compounds exemplified herein have typically been found to exhibit an $IC_{50}$ on the order of 30 micromolar or less in the test. For example, the compound described in Example 9 exhibits an $IC_{50}$ of 8.11 micromolar in the test. "$IC_{50}$" is a well understood term and means the concentration of test compound which causes a 50% decrease in the in vitro contraction of the bladder tissue described in the following test.

Male albino Hartley guinea pigs (450–500g) are sacrificed by carbon dioxide induced asphyxiation and quickly exsanguinated. The lower abdominal cavity is opened and the urinary bladder isolated. The bladder is cleaned of surrounding connective and adipose tissue, and the portion above the ureteral orifices is removed and washed in Krebs-Henseleit buffer solution of the following composition (in mm): NaCl 118.0, KCl 4.7, $MgSO_4$ 1.2, $KH_2PO_4$ 1.2, $CaCl_2$ 2.5, $NaHCO_3$ 25.0 and d-glucose 11.1. The solution is warmed to 37° C. and gassed with 95% $O_2$ and 5% $CO_2$. With vigorous bubbling, the solution should have a pH value close to 7.4.

The dome of the washed bladder is cut off and discarded; the remaining bladder is placed on a gauze in a Petri dish containing the buffer solution. A mid-ventral longitudinal cut is made with scissors to open the bladder. The strips cut from the dome and the base edge are discarded. The remaining detrusor mid-section is cut into two horizontal strips with an approximate width of 2.0 mm. These two strips are further bisected at the mid-dorsal section, creating four strip of similar dimensions. Each strip thus contains both dorsal and ventral portions of the bladder.

The two ends of each individual strip are tied to a glass support rod and a force-displacement transducer (Grass model FR03), respectively, with 4-0 black braided silk suture.

The transducers are connected to a polygraph (Grass model 7E), which is calibrated at 5 mV/cm and the calibration checked for linearity with weights of 5 and 0.5 grams. The analog electrical output signals from the polygraph are digitized by a Modular Instrument Micro 5000 signal processing system using Biowindow Data Acquisition Software, which is run under the Microsoft OS/2 operating system with an IBM-compatible PC.

The detrusor strips on the glass rod are secured in 20 ml tissue baths and allowed to equilibrate under a preload tension of 2 grams. During the following 45 to 60 min equilibration period, the tissue is washed with fresh buffer solution at 15 min interval, with the tension adjusted, if necessary, to 2 grams prior to washing. After the equilibration period, a priming dose of 15 mM KCl (total concentration in the bath) is applied. The tissue is washed after 10 min and washed twice more at 15 min intervals with tension adjusted to 2 grams before each washing.

When the tissue relaxes to a steady state after the final washing, 15 mM KCl is again applied. Once the myogenic activity of the tissue reaches a steady state, the baseline data are acquired through the Biowindows Data Acquisition System by averaging 5 min of the myogenic data sampled at 32 Hz. Once the baseline is acquired, the experimental compounds are dosed in a cumulative manner in half log unit increments. The contact time for each dose is 10 min with the final 5 min being the period of time that the dose reponse data are required. If 30 μM of the test compound does not abolished the detrusor mechanical activity, then 30 μM cromakalim, a putative potassium channel opener, is dosed to establish a maximum response. The effect of the compound at each dose is expressed as % of the maximum inhibitory response, which is further normalized with respect to the corresponding effect of the compound vehicle control. The normalized response is then used to derive the $IC_{50}$ of the relaxant activity of the compound through the application of Marquardt's nonlinear iterative curve fitting technique to a standard dose-response function.

The ability of compounds according to the invention to open potassium channels in detrusor smooth muscle can be further demonstrated by a second in vitro test.

This second in vitro test is similar to the one described above with regard to tissue preparation and data acquisition. However, the following exceptions are noted. In this second test, the contraction of the detrusor strips during priming and after the equilibration period is achieved with 80 mM instead of 15 mM KCl (total concentration in the bath). A sustained tension in the tissue is evident after this high KCl stimulation, because voltage-sensitive calcium channels have been rendered open to permit an influx of calcium into the cells and the development of tonic tension. This tension is totally abolished with 300 μM of papaverine, which is thereby used to establish the maximum response in this test.

Typical calcium channel blockers like nifedipine, nimodipine, isradipine, and verapamil are able to relax and reduce the myogenic activity of guinea pig detrusor strips in both tests by virtue of their blocking action on calcium channels. However, all of the aforementioned calcium channel blockers are more potent in the second test when 80 mM KCl is used, than in the first test where 15 mM KCl is used. In contrast, while the putative potassium channel opener cromakalim has a potent relaxant activity in the first test with an $IC_{50}$ in the range of 0.6 to 0.9 μM, it demonstrates insignificant relaxant activity in the second test at concentrations as high as 30 μM. Thus, the profile of a higher relaxant activity in the first test than in the second of compounds according to the invention indicates that the compounds are functioning as potassium channel openers.

The ability of the compounds according to the invention to act as potassium channel openers on bladder tissue may be further demonstrated by a standard test which measures the effect of test compounds on the rate of efflux of rubidium from the tissue.

It will be further appreciated by those skilled in the art that the efficacy of compounds according to the invention can be demonstrated by standard assays in vivo. The following is a description of such a standard test.

Male Wistar rats weighing 450–550 grams are anesthetized with 20 mg/kg, i.p. Nembutal and 80 mg/kg, i.p. Ketamine. The trachea is cannulated to prevent airway obstruction. Body temperature is maintained by means of a heating pad. Arterial blood pressure and heart rate may be measured with a pressure transducer connected to a polyethylene tube (PE50) which has been inserted into the right carotid artery. The right jugular vein is cannulated for drug administration. The urinary bladder is exposed through a midline abdominal incision and emptied of urine by application of slight manual pressure. A catheter (PE 50) is inserted through the apex of the bladder dome around 3–4 mm into its lumen and tied with suture (4-0 silk) to prevent leakage. The bladder catheter is connected to a pressure transducer for the measurement of bladder pressure. The bladder is then placed back into the abdominal cavity and the incision is stitched closed except where the catheter exits the cavity. The bladder is allowed to equilibrate for approximately 15 minutes. After the equilibration period, the rats are infused with saline directly into the bladder at a rate of 0.05 ml/min for the entire time of the experiment. The bladder pressure is then monitored for the start of bladder contractions. When the contractions start, the animal is then allowed to stabilize its pattern of contractions around 30 to 45 minutes before drug administration.

The test compounds are given i.v. The efficacy of a test compound is measured by comparison to the known reference drug cromakalim (SmithKline-Beecham) which is administered i.v. over the dose range of 0.05 to 0.5 mg/kg.

The above in vivo assay enables an assessment of both the blood pressure and cystometric activity of test compounds. Blood pressure is measured immediately after drug injection and at 5, 15 and 30 minutes later. Micturition contractions are induced by a slow continuous infusion of saline directly into the bladder. The average change (in seconds from control) in the duration of the intercontraction interval (the time between contractions) over an approximate 20-min period is reported for each compound.

The following is a description of a test in vivo which is complimentary to the above described tests and which can be used to ascertain if a test compound is active and, additionally, if the test compound exhibits selectivity for the bladder without significant cardiovascular effects when dosed orally. The compound described in Example 1 is active and selective in this test when dosed orally at 3 mg/kg body weight.

Male Wistar rats (400–500 g) were anesthetized with 50 mg/kg Nembutal, i.p. For each rat, the abdominal region and the front and back of the neck were shaved and povidone-iodine was applied to the skin. For carotid catheterization, the left carotid artery was exposed via a small ventral cervical incision. The exposed area was flushed with a 2% lidocaine HCl solution to relax the vessel. The catheter, filled with 0.9% saline, was introduced approximately 2.4 cm into the artery so that its tip resided in the aortic arch. The distal end of the catheter was exteriorized at the nape of the neck, filled with heparin (1000 units/ml) and heat sealed. For bladder catheterization, the bladder was exposed through a midline abdominal incision. A trocar was passed through the abdominal muscle about 1 cm from the upper end of the incision and then tunneled subcutaneously to emerge through the skin at the back of the neck. A saline-filled catheter was passed through the trocar. A small opening in the bladder dome was created with an Accu-Temp cautery. The catheter was placed into the bladder and secured with a 4-0 silk ligature. The catheter was flushed with saline and patency was noted. The external end of the catheter was heat-sealed to prevent urine leakage. The abdominal muscles and the skin were sutured. Both catheters were threaded through a stainless steel anchor button (Instech), which was then sutured to the subcutaneous muscle at the point of exteriorization. The skin was sutured closed over the button. The animals were allowed to recover from anesthesia.

24–48 hours after surgery, each rat was placed in a metabolism cage and connected via the anchor button to an Instech spring tether and swivel system to protect the catheters from damage and to allow the animal free movement in the cage. The carotid catheter was connected to a Gould P23XL pressure transducer for blood pressure measurement. The bladder catheter was connected to a pump for saline infusion and to a pressure transducer by means of PE50 tubing and a 4-way stopcock. A toploading balance with a collection cup was placed under the cage for urine output measurement.

The rats were weighed, orally sham-dosed (dosing needle introduced, but no fluid expelled), and transvesical saline infusion (0.18 ml/min) was begun and continued throughout the experiment. Variations in blood pressure, heart rate, intravesical pressure and urine output were recorded on either a Grass Polygraph or a Gould TA4000 recording system. The animals were allowed to equilibrate until the micturition pattern became consistent (approx. 45–90 min.). At this point, a basal level of each experimental parameter was recorded and the rats were administered by oral gavage the appropriate dose of compound (in a 75% PEG 400-saline vehicle) in concentrations such that the volume was 1 ml/kg body weight. The effects of the compounds on experimental parameters were followed for five hours after administration.

Experimental results for both the interval between contractions and also heart rates were expressed as the mean ±S.E.M. (Standard Error of Measures) % change from basal level, with each animal serving as its own control. MAP is expressed as mean +S.E.M mm Hg change from basal level.

Compounds according to the invention are active in one or more of the above-described tests.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography; reversed phase chromatography means flash chromatography over octadecylsilane (ODS) coated support having a particle diameter of 32–74μ, known as "PREP-40-ODS" (Art 731740-100 from Bodman Chemicals, Aston, Pa., USA); Thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; coupling constants (j) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the electron impact (EI) mode using a direct exposure probe; where indicated ionization was effected by chemical ionization (CI) or fast atom bombardment (FAB); values for m/z are given; generally, only ions which indicate the parent mass are reported.

EXAMPLE 1

2-Methyl-4-(3-nitrophenyl)-4,6,7,8-tetrahydro-5(1H)-quinolone.

2-Methyl-4-(3-nitrophenyl)-5-oxo-1,4,5,6,7,8-hexahydro-3-quinolinecarboxylic acid (4.66 g) was suspended in ethanol (200 mL) with concentrated sulfuric acid (0.5 mL). The mixture was heated at reflux for 5 h, during which time all of the solid went into solution. The solvent was evaporated, and the residue was partitioned between aqueous 2N sodium hydroxide and ethyl acetate. The aqueous portion was extracted with ethyl acetate. The combined extracts were washed (water, brine), dried, and evaporated to yield a residue which was purified by chromatography, eluting with ethyl acetate, to afford the title compound as a pale yellow solid (1.6 g); mp 183°–185° C.; MS: 284 (M); 250 MHz NMR: 1.76 (s,3, $CH_3$), 187 (m,2, $CH_2$), 2.16 (m,2, $CH_2$), 2.46 (m,2, $CH_2$), 4.58 (d,1, J=4.9, CH), 4.64 (d,1, J=4.9, CH), 7.53 (t,1, 7.6, Ar), 7.62 (d, 1, J=7.6, Ar), 7.96 (s,1, Ar), 7.98 (m,1, Ar), 8.80 (s,1, NH). Analysis for $C_{16}H_{16}N_2O_3$:Calculated: C, 67.59; H, 5.67; N, 9.85; Found: C, 67,44; H, 5.75; 9.56.

The starting 2-Methyl-4-(3-nitrophenyl)-5-oxo-1,4,5,6,7,8-hexahydro-3-quinolinecarboxylic acid was prepared as follows.

a. 2-Cyanoethyl 2-methyl-4-(3-nitrophenyl)-5-oxo-1,4,5,6,7,8-hexahydro-3-quinolinecarboxylate. 2-Cyanoethyl acetoacetate (4.27 g), 3-nitrobenzaldehyde (4.24 g), 1,3-cyclohexanedione (3.09 g) and ammonium acetate (4.26 g) were combined in ethanol (240 mL) and heated at reflux for 18 h. The solvent was evaporated and the residue was chromatographed, eluting with ethyl acetate, to afford the quinolinecarboxylate as a yellow solid (7.42 g); MS: 381 (M); 250 MHz NMR: 1.75–2.00 (m,2, $CH_2$), 2.22 (m,2, $CH_2$), 2.35 (s,3, $CH_3$), 2.81 (m,2, $CH_2$), 3.34 (m,2 $CH_2$), 4.12 (t,2, J=5.9, $CH_2$), 5.01 (s,1, CH), 7.51 (m,1, Ar), 7.84 (dd,1, J=7.7, 1.1, Ar), 7.97 (m,1, Ar), 7.99 (s,1, Ar), 9.43 (s,1, NH).

b. 2-Methyl-4-(3-nitrophenyl)-5-oxo-1,4,5,6,7,8-hexahydro-3-quinolinecarboxylic acid. To a suspension of 2-cyanoethyl 2-methyl-4-(3-nitrophenyl)-5-oxo-1,4,5,6,7,8-hexahydro-3-quinolinecarboxylate (0.47 g) in ethylene glycol dimethyl ether (2 mL) was added 1N sodium hydroxide (4 mL). The mixture was stirred for 20 h, during which time all of the solid went into solution. The mixture was diluted with water, washed with ethyl acetate, and acidified by addition of concentrated hydrochloric acid. The resulting precipitate was collected by vacuum filtration and dried to give the acid as a yellow solid (0.31 g); mp 253°–255° C.; MS: 328 (M); NMR: 1.63–2.00 (m,2, $CH_2$), 2.20 (m,2, $CH_2$), 2.31 (s,3, $CH_3$), 2.49 (m,2, $CH_2$), 5.0 (s,1, CH), 7.49–7.61 (m,2, Ar), 7.97 (m,2, Ar), 9.24 (s, 1, NH). Analysis for $C_{17}H_{16}N_2O_5$: Calculated: C, 62.19; H, 4.91; N, 8.53; Found: C, 62.16; H, 5.02; N, 8.33.

EXAMPLES 2–4

Except as otherwise indicated, the following 4-aryl-2-methyl-4,6,7,8-tetrahydro-5(1H)-quinolones of formula I, in which $R^4$ indicates the 4-aryl radical, were prepared from the corresponding 4-aryl-2-methyl-5-oxo-1,4,5,6,7,8-hexahydro-3-quinolinecarboxylic acids of formula III, using procedures similar to that described in Example 1, with exceptions as noted.

EXAMPLE 2

$R^4$=3-cyanophenyl; The product of Example 2.b. (1.10 g) was suspended in diethylene glycol (10 mL) and heated at 180° C. for 25 min. The reaction mixture was purified by chromatography, eluting with ethyl acetate, to provide the title compound as a pale yellow solid (0.52 g, 56%); mp 163°–165° C.; MS: 264 (M); NMR: 1.74 (s,3, $CH_3$), 1.86 (m,2, $CH_2$), 2.16 (m,2, $CH_2$), 2.44 (m,2, $CH_2$), 4.47 (d,1, J=4.8, CH) 4.60 (d,1, J=4.2, CH), 7.51 (m,4, At), 8.55 (s,1, NH). Analysis for $C_{17}H_{16}N_2O$. 0.15 $H_2O$: Calculated: C, 76.47; H, 6.14; N, 10.49; Found: C, 76.36; H, 6.17; N, 10.45.

EXAMPLE 3

$R^4$=3-bromo-4-fluorophenyl; Chromatography afforded a solid which was triturated with diethyl ether, filtered and dried to provided the title compound as a yellow solid (1.52 g); mp 177°–179° C.; MS: 336 (M); 400 MHz NMR: 1.74 (s,3, $CH_3$), 1.75–1.90 (m,2, $CH_2$), 2.14 (m,2, CH2), 2.43 (m,2, $CH_2$), 4.41 (d,1, J=4.7, CH), 4.58 (d,1, J=4.8, CH), 7.18 (m,2, Ar), 7.37 (dd,1, J=6.9, 2.0, Ar), 8,52 (s,1, NH). Analysis for $C_{16}H_{15}BrFNO$: Calculated C, 57.16; H, 4.50; N, 4.17; Found: C, 57.11; H, 4.61; 4.07.

EXAMPLE 4

$R^4$=4-fluorophenyl; the reaction mixture was evaporated and the residue was taken up in aqueous sodium bicarbonate and extracted with ethyl acetate. The combined organic extracts were washed (water, brine) and evaporated. The residue was chromatographed, eluting with ethyl acetate, providing an oil which solidified on standing. The solid was triturated with diethyl ether containing a few drops of ethyl acetate: Filtration and drying provided the title compound as a pale yellow solid (0.17 g); mp 170°–173° C.; MS: 257 (M); 250 MHz NMR: 1.72 (s,3, $CH_3$), 1.83 (m,2, $CH_2$), 2.13 (m,2, $CH_2$), 2.42 (m,2, $CH_2$) 4.38 (d,1, J=4.8, CH), 4.59 (d,1, J=4.9, CH), 7.04 (M,2, Ar), 7.14 (m,2, Ar), 8.45 (s,1, NH). Analysis for $C_{16}H_{16}FNO$: Calculated C, 74.69; H, 6.27; N, 5.44; Found: C, 74.45, H, 6.32; N, 5.34.

The starting 4-aryl-2-methyl-5-oxo-1,4,5,6,7,8-hexahydro-3-quinolinecarboxylic acids for Examples 2 and 3 were prepared as follows.

Except as otherwise indicated, the following 4-aryl-2-methyl-5-oxo-1,4,5,6,7,8-hexahydro- 3-quinolinecarboxylates of formula VIII in which Ra is 2-cyanoethyl and $R^4$ indicates the 4-aryl radical, were prepared from the corresponding benzaldehyde derivatives of formula $R^4CHO$ using procedures similar to that described in Example 1.a, eluting with the indicated chromatography solvent.

2.a. $R^4$=3-cyanophenyl; chromatography solvent: ethyl acetate; obtained as a pale yellow solid; MS: 361 (M); 250 MHz NMR: 1.70–2.00 (m,2, $CH_2$), 2.23 (m,2, $CH_2$), 2.35 (s,3, $CH_3$), 2.52 (m,2, $CH_2$), 2.82 (m,2, $CH_2$), 4.13 (t,2, J=5.7, $CH_2$), 4.94 (s,1, CH), 7.44 (m,1, Ar), 7.54 (m,3, Ar), 9.37 (s,1, NH).

3.a. $R^4$=3-bromo-4-fluorophenyl; chromatography solvent: ethyl acetate; obtained as a yellow solid (77%); MS: 433 (M); NMR: 1.67–2.00 (m,2, $CH_2$), 2.20 (m,2, $CH_2$), 2.32 (s,3, $CH_3$), 2.50 (m,2, $CH_2$), 2.82 (m,2, $CH_2$), 4.13 (t,2, J=5.9, $CH_2$), 4.87 (s,1, CH), 7.18 (m,2, Ar), 7.38 (d,1, J=6.1, Ar), 9.33 (s,1, NH).

4.a. $R^4$=4-fluorophenyl; chromatography solvent: ethyl acetate; obtained as a pale yellow solid (86%); MS, 354 (M) 250 MHz NMR: 1.63–2.00 (m,2, $CH_2$), 2.18 (m,2, $CH_2$), 2.29 (s,3, $CH_3$), 2.50 (m,2, $CH_2$), 2.81 (m,2, $CH_2$), 4.11 (t,2, J=5.4, $CH_2$), 4.87 (s,1, CH), 6.97 (t,2, J=8.8, Ar), 7.18 (m,2, Ar), 9.25 (s,1, NH).

Except as otherwise indicated, the following 4-aryl-2-methyl-5-oxo-1,4,5,6,7,8-hexahydro-3-quinolinecarboxylic acids of formula III, in which $R^4$ indicates the 4-aryl radical, were prepared by hydrolysis of the corresponding 2-cyanoethyl esters of formula VIII, described above, using procedures similar to that described in Example 1.b.

2.b. $R^4$=3-cyanoethyl; the reaction mixture was poured into ice water and as acidified with 1N hydrochloric acid. The resulting precipitate was collected by vacuum filtration and dried, providing the title compound as a pale yellow solid (95%); MS: 308 (M); NMR: 1.62–1.97 (m,2, $CH_2$), 2.19 (m,2, $CH_2$), 2.30 (s,3, $CH_3$), 2.49 (m,2, $CH_2$), 4.92 (s,1, CH), 7.47 (m,3, Ar), 7.56 (m,1, Ar), 9.17 (s,1, NH) 11.80 (broad s,1, $CO_2H$).

3.b. $R^4$=3-bromo-4-fluorophenyl; the reaction mixture was acidified with 6N hydrochloric acid. The resulting precipitate was collected by vacuum filtration and dried, providing the title compound as an off-white solid (69%); MS: 380 (M); 250 MHz NMR: 1.65–200 (m,2, $CH_2$), 2.21 (m,2, $CH_2$), 2.30 (s,3, $CH_3$), 2.51 (m,2, $CH_2$), 4.88 (s,1, CH), 7.20 (m,1, Ar), 7.36 (d,1, J=6.8, Ar), 9.17 (s,1, NH), 11.81 (broad s,1, $CO_2H$).

4.b. $R^4$=4-fluorophenyl; obtained as a white solid (94%); mp 235°–237° C. (dec); MS: 301 (M) 250 MHz NMR: 1.63–2.00 (m,2, $CH_2$), 2.19 (m,2, $CH_2$), 2.28 (s,3, $CH_3$), 2.47 (m,2, $CH_2$), 4.88 (s,1, CH), 7.00 (m,2, Ar), 7.15 (m,2, Ar), 9.09 (s,1, NH), 11.73 (broad s,1, $CO_2H$). Analysis for $C_{17}H_{16}FNO_3$: Calculated C,67.76; H, 5.35; N, 4.65; Found: C, 67.63; H, 5.35: N, 4.61

EXAMPLE 5

2-Methyl-4-phenyl-4,6,7,8-tetrahydro-5(1H)-quinolone.

trans-4-Phenyl-3-butene-2-one (1.63 g), 1,3-cyclohexanedione (1.30 g), and ammonium acetate (1.82 g) were combined in ethanol (100 mL) and heated at reflux for 5 h. The solvent was evaporated and the residue was chromatographed, eluting with ethyl acetate:hexane (2:1). A portion of the resulting solid was triturated with hot ethyl acetate, filtered, and dried to provide the tetrahydroquinolone as a pale yellow solid (0.53 g); mp 227°–229° C.; MS: 239 (M); 250 MHz NMR: 1.72 (s,3, $CH_3$), 1.73–1.95 (m,2, $CH_2$), 2.14 (m,2, $CH_2$), 2.43 (m,2, $CH_2$), 4.37 (d,1, J=4.8, CH), 4.60 (d,1 J=5.0, CH), 7.15 (m,5, Ar), 8.42 (s,1, NH). Analysis for $C_{16}H_{17}NO$: Calculated C, 80.30; H, 7.16; N, 5.85; Found: C, 80.16; H, 7.18; N, 5.76.

EXAMPLE 6

2-Methyl-4-(3,4-methylenedioxyphenyl)-4,6,7,8-tetrahydro-5(1H)-quinolone.

Using a procedure similar to that described in Example 5, but substituting 4-(3,4-Methylenedioxyphenyl)-3-butene-2-one for trans-4-Phenyl-3-butene-2-one, the title compound was prepared. Chromatography, eluting with ethyl acetate, provided a yellow solid. A second chromatography, eluting with acetonitrile:dichloromethane (20:80)gave a solid, which was triturated with diethyl ether to give the tetrahydroquinolone (13%) as a pale yellow solid; mp 217°–220° C.; MS: 283 (M), 250 MHz NMR: 1.72 (s,3, $CH_3$), 1.84 (m,2, $CH_2$), 2.11 (m,2, $CH_2$), 2.42 (m,2, $CH_2$), 4.30 (d, 1, J=4.7, CH), 4.57 (d,1, J=4.2, CH) 5.91 (s,2, $CH_2$), 6.58 (m,1, Ar), 6.65 (d,1, J=1.3, Ar), 6.73 (d,1, J=8.0, Ar), 8.42 (s,1, NH). Analysis for $C_{17}H_{17}NO_3 \cdot 0.1\ H_2O$: Calculated C, 71.62; H, 6.08; N, 4.91; Found: C, 71.59; H, 6.16; N, 5.27.

EXAMPLE 7

4-(4-Chlorophenyl)-2-methyl-4,6,7,8-tetrahydro-5(1H)-quinolone.

4-(4-Chlorophenyl)-3-butene-2-one (2.83 g), 1.3-cyclohexanedione (1.81 g), and ammonium acetate (2.60 g) were combined in ethanol (125 mL) and heated at reflux for 5.5 h. The solvent was evaporated, and the residue was taken up in water and extracted with ethyl acetate. The combined organic extracts were washed (water, brine), dried, and evaporated to yield a residue which was chromatographed, eluting with hexane:ethyl acetate (1:1) to yield the title compound as a pale yellow solid (1.46 g); mp 184°–187° C.; MS: 273 (M); NMR: 1.73 (s,3, $CH_3$), 1.75–1.98 (m,2, $CH_2$), 2.15 (m,2, $CH_2$), 2.43 (t,2, J=6.0, $CH_2$), 4.39 (d,1, J=4.7, CH), 4.58 (d,1,J=4.8, CH), 7.14 (d,2, J=8.4, Ar), 7.26 (d,2, J=8.4, Ar), 8.48 (s,1, NH); Analysis for $C_{16}H_{16}ClNO$: Calculated C, 70.20; H, 5.89; N, 5.12; Found: C, 70.21; H, 5.67; N, 5.02.

EXAMPLE 8

2-Methyl-4-(3-trifluoromethylphenyl)-4,6,7,8-tetrahydro-5(1H)-quinolone.

A mixture of 4-(3-trifluoromethylphenyl)-3-butene-2-one (4.9 g), 1,3-cyclohexanedione (2.68 g), ammonium acetate (2.65 g) and 75 mL of ethanol were heated at reflux for eight hours and then cooled to room temperature. The solvent was evaporated and the residue was partitioned between water and ethyl acetate. The organic layer was dried, filtered, and evaporated to yield a yellow solid. Recrystallization from ethyl acetate provided the title compound (2.8 g) as an off-white solid; mp 184°–185° C.; NMR: 1.74 (s,3, $CH_3$), 1.87–1.98 (m,2, $CH_2$), 2.13–2.19 (m,2, $CH_2$), 2.42–2.49 (m,2, $CH_2$) 4.50 (d,1, J=4.9, CH), 4.63 (d,1, J=4.9, CH), 7.45 (s,4, Ar), 8.53 (s,1, NH); (CI, $CH_4$) MS: m/z=308(M+1). Analysis for $C_{17}H_{16}F_3NO$: Calculated C, 66.44; H, 5.25; N, 4.56; Found: C, 65.90; H, 5.33; N, 4.43.

EXAMPLE 9

2-Methyl-4-(4-trifluoromethylphenyl)-4,6,7,8-tetrahydro-5(1H)-quinolone.

A mixture of 4-(4-trifluoromethyphenyl)-3-butene-2-one (4.9 g), 1,3-cyclohexanedione (2.68 g), ammonium acetate (2.65 g) and 75 mL of ethanol were heated at reflux for eight hours and then cooled to room temperature. The solvent was evaporated and the residue was partitioned between water and ethyl acetate. The organic layer was dried, filtered, and evaporated to obtain a yellow oil. Chromatography, with hexane:ethyl acetate (1:1) as the eluent, and recrystallization from toluene:hexane provided the title compound as a yellow solid (4.0 g); mp 116°–118° C.; NMR: 1.73 (s,3, $CH_3$), 1.87–1.98 (m,2, $CH_2$), 2.14–2.16 (m,2, $CH_2$), 2.45–2.49 (m,2, $CH_2$), 4.49 (d,1, J=4.9, CH), 4.60 (d,1, J=4.9, CH), 7.35 (d,2, J=8.0, Ar), 7.57 (d,2, J=8.0, Ar), 8.54 (s,1, NH); (CI, $CH_4$) MS: m/z=308(M+1); Analysis for $C_{17}H_{16}F_3NO$: Calculated C, 66.44; H, 5.25; N, 4.56; Found: C, 66.72; H, 5.34; N, 4.41.

EXAMPLE 10

4-(3-Chlorophenyl)-2-methyl-4,6,7,8-tetrahydro-5(1H)-quinolone.

A mixture of 4-(4-chlorophenyl)-3-butene-2-one (5.0 g), 1,3-cyclohexanedione (3.24 g), ammonium acetate (3.20 g) and 90 mL of ethanol were heated at reflux overnight and then cooled to room temperature. The solvent was evaporated and the residue was partitioned between water and ethyl acetate. The organic layer was dried, filtered, and evaporated to obtain a yellow solid. Recrystallization from ethanol provided the title compound as a yellow solid (3.0 g); mp 201°–203° C.; NMR: 1.73 (s,3, $CH_3$), 1.87–1.98 (m,2, $CH_2$), 2.13–2.17 (m,2, $CH_2$), 2.43–2.49 (m,2, $CH_2$), 4.40 (d,1, J=4.9, CH), 4.60 (d,1, J=4.9, CH), 7.09–7.25 (m,4, Ar), 8.50 (s,1, NH); (CI, $CH_4$) MS: m/z=274(M+1). Analysis for $C_{16}H_{16}ClNO \cdot 0.15\ H_2O$: Calculated C, 69.51; H; 5.94; N, 5.07; Found: C, 69.47; H, 6.03; N, 4.91.

EXAMPLE 11

2-Methyl-4-(4-methylphenyl)-4,6,7,8-tetrahydro-5(1H)-quinolone.

A mixture of 4-(4-methyphenyl)-3-butene-2-one (5.0 g), 1,3-cyclohexanedione (3.66 g), ammonium acetate (3.61 g) and 100 mL of ethanol were heated at reflux overnight and then cooled to room temperature. The solvent was evaporated and the residue was partitioned between water and ethyl acetate. The organic layer was dried, filtered, and evaporated to obtain an amber oil. Chromatography, with hexane:ethyl acetate (1:1) as the eluent, and trituration from ether provided the title compound as an off-white solid (2.0 g); mp 196°–198° C.; NMR: 1.73 (s,3, $CH_3$), 1.87–1.98 (m,2, $CH_2$), 2.14–2.16 (m,2, $CH_2$), 2.22 (s,3, $CH_3$), 2.43–2.49 (m,2, $CH_2$), 4.34 (d,1, CH), 4.57 (d,1, CH), 7.01 (s,4, Ar), 8.40 (s,1, NH); (CI, $CH_4$) MS: m/z=254(M+1). Analysis for $C_{17}H_{19}NO$: Calculated C, 80.60; H, 7.56; N, 5.53; Found: C, 80.24; H, 7.68; N, 5.36.

EXAMPLE 12

9-(3-Nitrophenyl)-3,4,5,6,7,8,9,10-octahydro-1(2H)-acridinone.

A mixture of 2-(3-nitrophenylmethylene)cyclohexanone (4.69 g), 1,3-cyclohexanedione (2.28 g), ammonium acetate (2.35 g) and 90 mL of ethanol was stirred at reflux under nitrogen for 48 hours. The mixture was cooled in an ice bath and orange crystals were collected by filtration. The material was chromatographed with dichloromethane, ethyl ether:dichloromethane (2:98) and ethyl ether:dichloromethane (10:90) as the elutents. The solvent was evaporated and the residue recrystallized from toluene/hexane to yield the title compound as yellow crystals (0.50 g); mp 218°–221° C.; NMR ($CDCl_3$): 1.57–1.59 (m,4, $CH_2$) 1.74–1.80 (m,2, $CH_2$) 1.88–2.01 (m,2, $CH_2$) 2.14 (broad s,2, $CH_2$) 2.28–2.36 (m,2, $CH_2$) 2.42–2.46 (m,2, $CH_2$) 4.50 (s,1, CH) 5.40 (s,1, NH) 7.38 (t,1, J=7.8, Ar) 7.71 (d,1, J=7.6, Ar) 7.98 (q,1, J=7.3, 1.4, Ar) 8.09 (d,1, J=1.9, Ar); MS (CI, $CH_4$): m/z=325(M+1). Analysis for $C_{19}H_{20}N_2O_3 \cdot 0.6\ H_2O$: Calculated C, 68.08; H, 6.37; N, 8.36; Found: C, 68.27; H, 6.28; N, 8.01.

The starting 2-(3-nitrophenylmethylene)cyclohexanone was prepared as follows.

1-Morpholino-1-cyclohexene (13.28 g) was added dropwise to a stirred solution of 3-nitrobenzaldehyde (10.0 g) and 65 mL of dry toluene, under nitrogen. After stirring at room temperature for 5 days the mixture was treated with 75 mL of 5N HCl, stirred an additional 15 minutes and the layers separated. The aqueous phase was extracted with three additional 75 mL portions of toluene, the toluene extracts were dried (MgSO$_4$), filtered and the solvent evaporated. The resulting yellow oil which turned greenish on standing overnight was chromatographed, with methylene chloride as elutent, to yield 2-($\alpha$-hydroxy-3-nitrobenzyl)cyclohexanone (6.35 g) as a yellow oil; MS (CI, CH$_4$): m/z=250(M+1). The yellow oil was dissolved in ethyl ether (50 mL) and treated with 50 mL of concentrated hydrochloric acid. After stirring overnight the layers were separated and the aqueous phase extracted with ethyl ether. The combined extracts were dried (MgSO$_4$), filtered and evaporated to yield crude 2-(3-nitrophenyl)methylenecyclohexanone as low melting orange crystals (4.69 g), which were used without further purification. NMR CDCl$_3$): 1.79–1.89 (m,2, CH$_2$), 1.93–2.01 (m,2, CH$_2$), 2.56–2.60 (m,2, CH$_2$), 2.82–2.87 (m,2, CH$_2$), 7.47 (s,1, olefinic), 7.58 (t,1, J=7.9, Ar), 7.69 (d,1, J=7.7, Ar), 8.19 (d,1, J=8.9, Ar), 8.24 (s,1, Ar); MS (CI, CH$_4$): m/z=232(M+1).

EXAMPLE 13

9-(3-Cyanophenyl)-3,4,5,6,7,8,9,10-octahydro-1(2H)-acridineone.

A mixture of 9-(3-cyanophenyl)-3,4,6,7,9,10-hexahydro-1,8-(2H,5H)-acridinedione (3.18 g), sodium borohydride (2.50 g) and 50 mL of ethanol was stirred at 70° C. overnight. The mixture was treated with abut 300 mL of water, stirred for several hours and the solid collected by suction filtration, slurried on the funnel with a little ethanol and sucked dry on the funnel. The solid (1.87 g) was combined with 0.49 g of material from a previous run and the combined material was chromatographed, with methanol:dichloromethane (2.5:97.5) as elutent. The solvent evaporated and the residue taken up in 50 mL of methanol and about 20 mL of methylene chloride. The solution was concentrated on a steam bath until crystals started to form, was treated with an equal volume of ethyl acetate and refrigerated overnight. The title compound was obtained as bright yellow crystals (1.16 g); mp 246°–249° C.; NMR: 1.47 (broad s,2, CH$_2$), 1.65–1.87 (m,6, CH$_2$), 2.11 (m,4, CH$_2$), 2.39–2.51 (m,2, CH$_2$), 4.25 (s,1, CH), 7.41–7.57 (m,4, Ar), 8.45 (s,1, NH); (CI, CH$_4$) MS: m/z=305(M+1). Analysis for C$_{20}$H$_{20}$N$_2$O: Calculated C, 78.92; H, 6.62; N, 9.20; Found: C, 78.64; H, 6.65; N, 9.08.

The intermediate 9-(3-cyanophenyl)-3,4,6,7,9,10-hexahydro-1,8-(2H,5H)-acridineone can be prepared as follows.

A stirred mixture of 3-cyanobenzaldehyde (1.48 g), 1,3-cyclohexanedione (2.53 g) and ammonium acetate (1.24 g) in ethanol (20 mL) was refluxed for 18 hours. The mixture was poured into water, and the yellow solid collected and dried under vacuum to yield the title acridinedione (3.22 g); mp 285°–288° C.; NMR: 1.80–1.93 (m,4) 2.19–2.22 (m,4) 2.50–2.54 (m,4) 4.91 (s,1) 7.37–7.42 (m,1) 7.48–7.54 (m,3) 9.55 (s,1); MS: m/z=319 (M+1). Analysis for C$_{20}$H$_{18}$N$_2$O$_2$: Calculated C, 75.44; H, 5.71; N, 8.80. Found: C,75.27; H, 5.66; N, 8.77.

EXAMPLE 14

2-Isobutyl-4-phenyl-4,6,7,8-tetrahydro-5(1H)-quinolone.

5-Methyl-1-phenyl-1-hexen-3-one (5.05 g), 1,3-cyclohexanedione (3.31 g) and ammonium acetate (4.91 g) were combined in 200 mL of ethanol and allowed to reflux for 7 hours. The mixture was evaporated and the residue was purified by chromatography, with ethyl acetate as the eluent, to provide the title compound as a white solid (1.48 g); mp 182°–184° C.; MS: 281 (M); NMR: 0.79 (d,3, J=5.5, CH$_3$), 0.85 (d,3, J=5.5, CH$_3$), 1.73–1.93 (m,5, CH$_2$, CH$_2$, CH), 2.13 (m,2, CH$_2$), 2.42 (m,2, CH$_2$), 4.38 (d,1, J=4.9, CH), 4.58 (d,1, J=5.0, CH), 7.03–7.23 (m,5, Ar), 8.30 (s,1, NH). Analysis for C$_{19}$H$_{23}$NO: Calculated C, 81.80; H, 8.24; N, 4.98; Found: C, 80.91; H, 8.21; N, 5.00.

EXAMPLE 15

2-Trifluoromethyl-4-(3-nitrophenyl)-4,6,7,8-tetrahydro-5(1H)quinolone.

A suspension of 3-carboxy-2-trifluoromethyl-2-hydroxy-4-(3-nitrophenyl)-4,6,7,8-tetrahydro- 5(1H)-quinolone (3.17 g) in toluene (150 mL) was treated with p-toluenesulfonic acid monohydrate (0.32 g), the mixture refluxed vigorously under Dean-Stark conditions for 4 hours and then partitioned between water and ethyl acetate. The organic phase was washed (water and brine) and evaporated. The residue was purified by chromatography (hexane/ethyl acetate, 1:1 and methylene chloride/acetonitrile 95:5) to yield the title compound (0.83 g) as a pale yellow solid; mp 215°–216° C.; NMR: 1.77–2.00 (m,2, CH$_2$), 2.16–2.36 (m,2, CH$_2$), 2.50–2.71 (m,2, CH$_2$), 4.79 (d,1, J=4.1, CH), 5.67 (d,1, J=5.4, CH), 7.57–7.67 (m,2, Ar), 8.04 (m,2, Ar), 9.48 (s,1, NH); MS: m/z=338(M). Analysis for C$_{16}$H$_{13}$F$_3$N$_2$O$_3$: Calculated C, 56.81; H, 3.87; N, 8.28; Found: C, 56.74; H, 4.02; N, 8.28.

The starting 3-carboxy-2-trifluoromethyl-2-hydroxy-4-(3-nitrophenyl)-4,6,7,8-tetrahydro- 5(1H)-quinolone was obtained as follows:

A stirred mixture of ethyl 4,4,4-trifluoroacetoacetate (6.00 mL), 1,3-cylohexanedione (4.65 g), 3-nitrobenzaldehyde (6.31 g), and ammonium acetate (6.57 g) in ethanol (350 mL) was heated at reflux for 4.5 hours. After removal of solvent the orange residue was treated diethyl ether, and the resulting precipitate was collected by filtration. The solid was triturated with hot diethyl ether, collected, and purified by chromatography (ethyl acetate) to yield 3-carboethoxy-2-trifluoromethyl-2-hydroxy-4-(3-nitrophenyl)-4,6,7,8-tetrahydro-5(1H)-quinolone (8.47 g) as a white solid. NMR: 0.85 (t,3, J=7.1, CH$_3$), 1.86 (m,2, CH$_2$), 2.07 (m,2, CH$_2$), 2.27–2.44 (m,1, CH$_2$), 2.57–2.72 (m,1, CH$_2$), 2.75 (d,1, J=11.9, CH), 3.83 (m,2, CH$_2$), 4.07 (d,1, J=11.4, CH), 7.30 (s,1, OH), 7.50 (m,1, Ar), 7.57 (m,1, Ar), 7.87 (m,1, Ar), 8.01 (m,1, Ar), 8.16 (s,1, NH); MS: m/z=428(M).

A suspension of 3-carboethoxy-2-trifluoromethyl-2-hydroxy-4-(3-nitrophenyl)-2,3,4,6,7,8-hexahydro- 5(1H)-quinolone (7.02 g) in ethanol (40 ml) and water (40 ml) was treated with lithium hydroxide monohydrate (1.44 g). The mixture was heated at 90° C. for 30 minutes, diluted with water, acidified with 1N hydrochloric acid, and extracted with ethyl acetate. The combined organic extracts were washed (water and brine), dried, filtered and the solvent stripped to yield a brown oil which was further purified by chromatography (ethyl acetate and ethyl acetate/methanol, 4:1). 3-Carboxy-2-trifluoromethyl-2-hydroxy-4-(3-nitrophenyl)- 4,6,7,8-tetrahydro-5(1H)-quinolone (2.07 g) was obtained as a white solid. NMR: 1.85 (m,2, CH$_2$), 2.10 (m,2, CH$_2$), 2.33–2.60 (m,3, CH$_2$, CH), 4.21 (d,1, J=8.7, CH), 7.47 (m,2, Ar), 7.81 (s,2, OH or NH, Ar), 7.96 (m,1H, Ar); MS: m/z=400(M).

EXAMPLE 16

2,7,7-Trimethyl-4-(3-nitrophenyl)-4,6,7,8-tetrahydro-5(1H)quinolone.

4-(3-Nitrophenyl)-3-buten-2-one (0.87 g), 5,5-dimethyl-1,3-cyclohexanedione (0.66 g) and ammonium acetate (0.82 g) were combined in ethanol (30 mL) and heated at reflux for 6.5 hours. After removal of solvent and chromatography (hexane/ethyl acetate; 1:1) the title compound (1.02 g) was obtained as a yellow solid; mp 162°–164° C.; NMR: 0.94 (s,3, $CH_3$), 1.01 (s,3, $CH_3$), 1.76 (s,3, $CH_3$), 1.90–2.18 (m,2, $CH_2$), 2.25–2.43 (m,2, $CH_2$), 4.55 (d,1, J=4.7, CH), 4.64 (d,1, J=4.8, CH), 7.54 (m,1, Ar), 7.63 (m,1, Ar), 7.96 (s,1, Ar), 7.97 (m,1, Ar), 8.53 (s,1, NH); MS: m/z=312(M). Analysis for $C_{18}H_{20}N_2O_3$: Calculated C, 69.21; H, 6.45; N, 8.97; Found: C, 69.07; H, 6.56; N, 8.85.

The starting 4-(3-Nitrophenyl)-3-buten-2-one was prepared as follows:

2N Sodium hydroxide (2.4 mL) was added dropwise at 5°–10° C. to a precooled (5°–10 C.) stirred solution of 3-nitrobenzaldehyde (10.04 g) in acetone (50 mL). The mixture was warmed to room temperature, stirred for 20 minutes, diluted with water, acidified with 2N hydrochloric acid and extracted with ethyl acetate. The combined organic extracts were washed (water and brine) and dried. Chromatography of the resulting orange oil (methylene chloride) gave the title compound (2.73 g) as a pale yellow solid. NMR: 2.37 (s,3, $CH_3$), 7.01 (d,1, J=16.0, CH), 7.73 (m,1, Ar), 7.78 (d,1, J=16.2, CH), 8.20 (d,1, J=7.9, Ar), 8.26 (m,1, Ar), 8.55 (s,1, Ar); MS: m/z=191(M).

EXAMPLE 17

4-(3-Chlorophenyl)-2,7,7-trimethyl-4,6,7,8-tetrahydro-5(1H)quinolone.

A mixture of 4-(3-chlorophenyl)but-3-en-2-one (5.0 g), 5,5-dimethyl-1,3-cyclohexanedione (3.88 g), ammonium acetate (3.20 g) and ethanol (90 mL) was heated at reflux for ten hours. The reaction mixture was worked up as described in Example 8 and recrystallization from ethyl acetate-hexane yielded the title compound (4.7 g) as a light yellow solid, mp 183°–185° C.; NMR: 0.94(s,3, $CH_3$), 1.00 (s,3, $CH_3$), 1.74 (s,3, $CH_3$), 1.95 (d,1, J=16, CH), 2.11 (d,1, J=16, CH), 2.25 (d,1, J=16.7, CH), 2.35 (d,1, J=16.7, CH), 4.38 (d,1, J=4.6, CH), 4.59 (d,1, J=4.6, CH), 7.09–7.28 (m,4, Ar), 8.44 (s,1, NH); (CI, $CH_4$) MS: m/z=302(M+1). Analysis for $C_{18}H_{20}ClNO$: Calculated C, 71.63; H, 6.68; N, 4.64; Found: C, 71.60; H, 6.69; N, 4.54.

EXAMPLE 18

2-Ethyl-4-(3-nitrophenyl)-4,6,7,8-tetrahydro-5(1H)-quinolone.

A mixture of 1-(3-nitrophenyl)-1-penten-3-one (2.42 g), 1,3-cyclohexanedione (1.36 g), ammonium acetate (2.00 g) and ethanol (70 mL) was heated at reflux for 7.5 hours. Removal of solvent, chromatography (ethyl acetate/hexane, 2:1 and methylene chloride/acetonitrile, 9:1), trituration with hot diethyl ether and recrystallization from ethyl acetate provided the title compound (1.29 g) as a yellow solid; mp 182°–184° C.; NMR: 1.03 (t,3, J=7.4, $CH_3$), 1.70–1.95 (m,2, $CH_2$), 2.07 (q,2, J=7.5, $CH_2$), 2.17 (m,2, $CH_2$), 2.48 (m,2, $CH_2$), 4.59 (d,1, J=4.8, CH), 4.66 (dd, 1, J=4.8, 0.9, CH), 7.53 (m,1, Ar), 7.64 (m,1, Ar), 7.98 (m,2, Ar), 8.55 (s,1, NH). MS: m/z=298(M). Analysis for $C_{17}H_{18}N_2O_3$: Calculated: C., 68.44; H, 6.08; N, 9.39; Found: C, 68.43; H, 6.09; N, 9.39.

The starting 1-(3-Nitrophenyl)-1-penten-3-one was prepared as follows:

2-Butanone (3.90 mL) was added to a mixture of pyrrolidine (3.70 mL) and glacial acetic acid (2.50 mL) at 5° C. The cooling bath was removed, and a solution of 3-nitrobenzaldehyde (6.70 g) in toluene (30 ml) and diethyl ether (10 ml), was added dropwise to the mixture. Stirring was continued at room temperature for 48 hours. The reaction mixture was partitioned between water and ethyl acetate and acidified with 2N hydrochloric acid until the aqueous portion remained acidic. The organic portion was washed (water and brine) dried, the solvent stripped and the resulting brown solid chromatographed (hexane/ethyl acetate 2:1). Trituration with hexane/ethyl acetate gave the title compound (2.45 g) as a yellow solid; NMR: 1.04 (t,3, J=7.3, $CH_3$), 2.75 (q,2, J=7.3, $CH_2$), 7.10 (d,1, J=16.3, CH), 7.72 (m,1, Ar), 7.74 (d,1, J=16.3, CH), 8.20 (m,1, Ar), 8.25 (m,1, Ar), 8.56 (m,1, Ar); MS: m/z=205(M).

EXAMPLE 19

2-Isopropyl-4-(3-nitrophenyl)-4,6,7,8-tetrahydro-5(1H)-quinolone.

4-Methyl-1-(3-nitrophenyl)-1-penten-3-one (2.90 g), 1,3-cyclohexanedione (1.50 g), and ammonium acetate (2.14 g) were combined in ethanol (100 mL) and heated at reflux for 7 hours. After removal of solvent, chromatography (hexane/ethyl acetate; 1:1) and trituration with diethyl ether the title compound (1.63 g) was obtained as a yellow solid; mp 195°–196°C.; NMR: 1.06 (d,3, J=6.9, $CH_3$), 1.07 (d,3, J=6.9, $CH_3$), 1.67–1.95 (m,2, $CH_2$), 2.07–2.22 (m,2, $CH_2$), 2.33 (m,1, CH), 2.49 (m,2, $CH_2$), 4.60 (d,1, J=5.0, CH), 4.67 (d,1, J=4.9, CH), 7.53 (m,1, Ar), 7.64 (m,1, Ar), 7.97 (m,2, Ar), 8.42 (s,1, NH); MS: m/z=312(M). Analysis for $C_{18}H_{20}N_2O_3$: Calculated C, 69.21; H, 6.45; N, 8.97; Found: C, 69.03; H, 6.50; N, 8.60.

The starting 4-methyl-1-(3-nitrophenyl)-1-penten-3-one was obtained as follows:

3-Methyl-2-butanone (5.00 mL) was added to a mixture of pyrrolidine (3.40 mL) and glacial acetic acid (2.30 mL) at 5° C. The cooling bath was removed and a solution of 3-nitrobenzaldehyde (6.16 g) in toluene (30 mL) and diethyl ether (10 mL) was added dropwise to the mixture. After 48 hours at room temperature, the mixture was poured into 2N HCl and extracted with ethyl acetate. The organic phase was washed (water and brine), dried and the solvent removed. Purification by chromatography (hexane/ethyl acetate, 3:1) gave 1-hydroxy-4-methyl-1-(3-nitrophenyl)pentan-3-one (3.95 g) as a yellow solid. NMR: 0.96 (d,3, J=6.9, $CH_3$), 1.00 (d,3, J=6.9, $CH_3$), 2.62 (m,1, CH), 2.73–2.97 (m,2, $CH_2$), 5.14 (m,1, CH), 5.66 (d,1, J=4.7, OH), 7.62 (m,1,Ar),7.81 (d,1, J=7.7, Ar), 8.11 (m,1, Ar),8.23 m,1, Ar); (CI, $CH_4$) MS: m/z=238(M+1).

A mixture of 1-hydroxy-4-methyl-1-(3-nitrophenyl)pentan--3-one (3.32 g), p-toluenesulfonic acid monohydrate (0.03 g) and toluene (50 mL) was refluxed for 1 hour under Dean-Stark conditions. The mixture was diluted with ethyl acetate, washed (sat. sodium bicarbonate, water and brine) and the solvent removed. Chromatography (hexane/ethyl acetate, 3:1) yielded 4-methyl-1-(3-nitrophenyl)-1-penten-3-one (2.98 g) as a yellow solid. NMR: 1.11 (d,6, J=6.8, $CH_3$), 3.02 (m,1, CH), 7.27 (d,1, J=16.2, CH), 7.73 (m,2, CH,Ar), 8.24 (m,2, Ar), 8.61 (m,1, Ar), MS: m/z=219(M).

EXAMPLE 20

2-(t-Butyl)-4-(3-nitrophenyl)-4,6,7,8-tetrahydro-5(1H)-quinolone.

t-Butyl-3-nitrostyrylketone (1.81 g), 1,3-cyclohexanedione (0.82 g), and ammonium acetate (1.25 g) were combined in ethanol (50 mL) and heated at reflux for 7.5 hours. Following removal of solvent and chromatography (hexane/ ethyl acetate; 1:1 and methylene chloride/acetonitrile 9:1) the title compound (0.54 g) was obtained as a yellow solid; mp 180°–181.5°C.; NMR: 1.12 (s,9, CH$_3$), 1.68–1.95 (m,2, CH$_2$), 2.06–2.27 (m,2, CH$_2$), 2.42–2.67 (m,2, CH$_2$), 4.61 (d,1, J=5.2, CH), 4.72 (dd,1, J=5.2, 1.8; CH), 7.53 (m,1, Ar), 7.64 (m,1, Ar), 7.97 (m,2, Ar), 8.10 (s,1, NH); MS: m/z= 326(M). Analysis for C$_{19}$H$_{22}$N$_2$O$_3$: Calculated C, 69.92; H, 6.79; N, 8.58; Found: C, 69.96; H, 6.80; N, 8.60.

EXAMPLE 21

4-(3,4-Dichlorophenyl)-2-methyl-4,6,7,8-tetrahydro-5(1H)-quinolone.

A mixture of 1-(3,4-dichlorophenyl)but-1-en-3-one (5.0 g), 1,3-cyclohexanedione (2.71 g), ammonium acetate (2.70 g) and ethanol (75 mL) was heated at reflux for ten hours. The reaction was worked up as described in Example 8, and recrystallization from ethyl acetate-hexane yielded the title compound (2.6 g) as an off-white solid, mp 199°–201° C.; NMR: 1.74 (s,3, CH$_3$), 1.84–1.88 (m,2, CH$_2$), 2.14–2.19 (m,2, CH$_2$), 2.41–2.46 (m,2, CH$_2$), 4.42 (d,1, J=4.7, CH), 4.59 (d,1, J=4.7, CH), 7.12 (dd,1, J=8.3,2.0, Ar), 7.31 (d,1, J=2.0, Ar), 7.48 (d,1, J=8.3, Ar), 8.55 (s,1, NH); (CI, CH$_4$) MS: m/z=308(M+1). Analysis for C$_{16}$H$_{15}$Cl$_2$NO: Calculated C, 62.35; H, 4.91; N, 4.54; Found: C, 62.03; H, 5.09; N, 4.44.

EXAMPLE 22

4-(3-Methoxyphenyl)-2-methyl-4,6,7,8-tetrahydro-5(1H)-quinolone.

A solution of 1-(3-methoxyphenyl)but-1-en-3-one (2.07 g), 1,3-cyclohexanedione (1.37 g) and ammonium acetate (1.39 g) in ethanol (20 mL) was stirred at reflux for 10 hours. The reaction was worked up as described in Example 8 and purified by chromatography (10% v/v ethyl ether in methylene chloride) to yield the title compound (1.14 g) as an off-white solid. Recrystallization from ethanol/hexane gave analytically pure material, mp 164°–167° C.; NMR: 1.71 (s,3, CH$_3$), 1.82–1.88 (m,2, CH$_2$), 2.13–2.17 (m,2, CH$_2$), 2.40–2.44 (m,2, CH$_2$), 3.67 (s,3, CH$_3$), 4.35 (d,1, J=4.8, CH), 4.60 (d,1, J=4.6, CH), 6.64–6.66 (m,2, Ar), 6.71 (d,1, J=7.7, Ar), 7.12 (dd,1, J=7.7, 3.8, Ar), 8.41 (s,1, NH); (CI, CH$_4$)MS: m/z=270(M+1). Analysis for C$_{17}$H$_{19}$NO$_2$.0.5H$_2$O: Calculated C, 73.36; H, 7.24; N, 5.03. Found: C, 73.49; H, 6.98; N, 4.93.

EXAMPLE 23

3-Acetyl-2-methyl-4-(3-nitrophenyl)-4,6,7,8-tetrahydro-5(1H)-quinolone.

4-Amino-3-penten-2-one (2.00 g), 1,3-cyclohexanedione (2.30 g), and 3-nitrobenzaldehyde (3.08 g) were combined in ethanol (180 mL) and heated at reflux for 5 hours. A yellow solid formed upon cooling to ambient temperature. The solid was purified by trituration with hot ethyl acetate/ethanol to yield the title compound (2.65 g) as a yellow solid; mp >250° C.; NMR: 1.67–1.97 (m,2, CH$_2$), 2.13 (s,3, CH$_3$), 2.22 (m,2, CH$_2$), 2.35 (s,3, CH$_3$), 2.47 (m,2, CH$_2$), 5.11 (s,1, CH), 7.52 (m,1, Ar), 7.60 (d,1, J=7.7, Ar), 7.97 (m,2, Ar), 9.32 (s,1, NH); MS: m/z=326(M). Analysis for C$_{18}$H$_{18}$N$_2$O$_4$: Calculated C, 66.25; H, 5.56; N, 8.58, Found: C, 65.99; H, 5.61; N, 8.40.

EXAMPLE 24

2-(Isobutyl)-4-(3-nitrophenyl)-4,6,7,8-tetrahydro-5(1H)quinolone.

A solution of 5-methyl-1-(3-nitrophenyl)-1-hexen-3-one (2.52 g), 1,3-cyclohexanedione (1.22 g) and ammonium acetate (1.88 g) in ethanol (65 mL) was stirred at reflux for 7.5 hours. After removal of the solvent, the residue was chromatographed (ethyl acetate/hexane 2:1) to yield the title compound (1.51 g) as a yellow solid; mp 158°–160° C.; NMR: 0.81 (d,3, J=5.8, CH$_3$), 0.86 (d,3, J=5.8, CH$_3$), 1.77–1.97 (m,5, CH$_2$, CH), 2.10–2.23 (m,2, CH$_2$), 2.46 (m,2, CH$_2$), 4.59(d,1,J=4.8, CH), 4.64 (d,1, J=5.8, CH), 7.53 (m,1, Ar), 7.65 (m,1, Ar), 7.97 (m,2, Ar), 8.49 (s,1, NH); MS: m/z=326(M). Analysis for C$_{19}$H$_{22}$N$_2$O$_3$: Calculated C, 69.92; H, 6.79; N, 8.58; Found: C, 70.03; H, 6.81; N, 8.54.

The starting 5-methyl-1-(3-nitrophenyl)-1-hexen-3-one was obtained as follows:

4Methyl-2-pentanone (5.00 mL) was added to a mixture of pyrrolidine (3.30 mL) and glacial acetic acid (2.30 mL) at 5° C. The cooling bath was removed, and a solution of 3-nitrobenzaldehyde (6.12 g) in toluene (25 mL) and diethyl ether (10 mL) was added dropwise to the mixture. After 48 hours at room temperature, the reaction mixture was diluted with water, acidified with 2N hydrochloric acid and extracted with ethyl acetate. The combined organics were washed (water and brine), dried and the resulting oily residue purified by chromatography (hexane/ethyl acetate, 3:1) to yield the title compound (5.42 g) as a pale yellow solid. NMR: 0.92 (d,3, J=6.6, CH$_3$), 0.93 (d,3, J=6.6, CH$_3$), 2.14 (m,1, CH), 2.60 (d,2, J=7.0, CH), 7.09 (d,1, J=16.4, CH,), 7.72 (m,1, Ar), 7.75 (d,1, J=16.0, CH), 8.20 (d,1, J=7.9, Ar), 8.25 (m,1, Ar), 8.57 (s, 1, Ar); MS: m/z=233(M)

EXAMPLE 25

9-(3-Nitrophenyl)-3,4,5,6,7,8,9,10-octahydro-1(2H)-acridinone.

To a mixture of 9-(3-nitrophenyl)-3,4,6,7,9,10-hexahydro-1,8(2H,5H)-acridinedione (3.00 g) in ethanol (30 mL) was added sodium borohydride (2.21 g) in ethanol (20 mL). The mixture was heated at reflux for 16 hours, cooled, and additional sodium borohydride (1.11 g) was added. After an additional hour at reflux the reaction was filtered while hot and the filtrate diluted with water. Ethanol was removed and the aqueous portion extracted with ethyl acetate (2×150 mL). The combined organics were dried, concentrated to a brown oil and chromatographed (5–10% ethyl ether/methylene chloride) to yield the title acridinone as a yellow solid (1.12 g), mp 218°–220° C.; NMR: 1.46–1.52 (m,3, CH$_2$), 1.62–1.98 (m,5, CH$_2$), 2.05–2.19 (m,4, CH$_2$) 2.40–2.46 (m,2, CH$_2$), 4.35 (s,1, CH), 7.49–7.55 m,1, Ar), 7.61–7.65 (m,1, Ar), 7.95–7.99 (m,2, Ar), 8.52 (s,1, NH); (CI, CH$_4$) MS: m/z=325(M+1). Analysis for C$_{19}$H$_{20}$N$_2$O$_3$: Calculated C, 70.35; H, 6.21; N, 8.64; Found: C, 70.06; H, 6.25; ,; 8.34.

A preparation of the necessary acridinedione starting material is described in German patent application publication number DE 2003148.

EXAMPLE 26

9-(3-Methoxyphenyl) -3,4,5,6,7,8,9,10-octahydro-1(2H)-acridinone.

To a mixture of 9-(3-methoxyphenyl)-3,4,6,7,9,10-hexahydro-1,8(2H,5H)-acridinedione (5.75 g) in ethanol (150 mL) was added sodium borohydride (4.04 g). The mixture was heated at reflux for 16 hours, cooled and additional sodium borohydride (2.69 g) was added. The mixture was heated at reflux for 8 hours, cooled and additional sodium borohydride (3.50 g) was added. The mixture was heated at reflux for 16 hours, poured into water and filtered to yield an off-white solid. Recrystallization from ethanol yielded the title acridinone as a white solid (5.36 g), mp 240°–242° C.; NMR: 1.46–1.52 (m,3, $CH_2$), 1.64–1.87 (m,5, $CH_2$), 2.08–2.13 (m,4, $CH_2$), 2.37–2.43 (m,2, $CH_2$), 3.68 (s,3, $CH_3$), 4.12 (s,1, CH), 6.63–6.74 (m,3, Ar), 7.10 (t,1, J=7.76, Ar), 8.34 (s,1, NH); (CI, $CH_4$) MS: m/z= 310(M+1). Analysis for $C_{20}H_{23}NO_2 \cdot 0.50H_2O$: Calculated C, 75.44; H, 7.59; N, 4.40; Found: C, 75.20; H, 7.30; N, 4.37.

The necessary acridinedione starting material may be prepared according to the method described in S. M. Jain et al, Indian Journal of Chemistry, Volume 30B, November 1991, pages 1037–1040.

EXAMPLE 27

9-(3-Trifluoromethoxyphenyl)-3,4,5,6,7,8,9,10-octahydro-1(1(2H)acridinone.

To a mixture of 9-(3-trifluoromethoxyphenyl)-3,4,6,7,9,10-hexahydro-1,8(2H,5H)-acridinedione (2.70 g), ethanol (25 mL) and dimethylformamide (15 mL) was added sodium borohydride (1.62 g). The mixture was heated at reflux for 16 hours, cooled and additional sodium borohydride (1.62 g) was added. The mixture was heated at reflux for 2 hours, cooled and additional sodium borohydride (2.00 g) was added. The mixture was heated at reflux for 2 hours, poured into water and filtered to yield an off-white solid. Purification by chromatography (5% ethyl-acetate/methylene chloride) yielded the title acridinone as a white solid (1.41 g), mp 214°–216° C. NMR: 1.46–1.52 (m,3, $CH_2$), 1.65–1.88 (m,5, $CH_2$), 2.08–2.14 (m,4, $CH_2$), 2.38–2.43 (m,2, $CH_2$), 4.23 (s,1, CH), 7.06 (m,2, Ar), 7.18 (d,1, J=7.73, Ar), 7.33 (m,1, Ar), 8.44 (s,1, NH); (CI, $CH_4$) MS: m/z=364(M+1). Analysis for $C_{20}H_{20}NO_2F_3 \cdot 0.20H_2O$: Calculated C, 65.46; H, 5.60; N, 3.82; Found: C, 65.42; H, 5.53; N, 3.62.

The necessary acridinedione starting material may be prepared following the method described in Example 28 hereinbelow, but using 3-trifluoromethoxybenzaldehyde in place of 3-trifluoromethylbenzaldehyde. M.p. 273°–275° C. Found for $C_{20}H_{18}FNO_3$: C,63.55; H,4.71; N, 3.67.

EXAMPLE 28

9-(3-Trifluoromethylphenyl)-3,4,5,6,7,8,9,10-octahydro-1(2H )-acridinone.

A mixture of 9-(3-trifluoromethylphenyl)-3,4,6,7,9,10-hexahydro-1,8(2H,5H)-acridinedione (2.0 g), sodium borohydride (2.1 g) and ethanol (50 mL) was heated at 70° C. overnight and cooled to room temperature. The mixture was partitioned between water and ethyl acetate; the organic layer dried, filtered and concentrated. Chromatography (eluant: methylene chloride/methanol; 98/2) and recrystallization from ethanol/hexane provided the title compound (1.0 g) as a yellow solid, m.p. 250°–251° C.; NMR: 1.47–1.52 (m,3, $CH_2$), 1.66–1.90 (m,5, $CH_2$), 2.10–2.15 (m,4, $CH_2$), 2.40–2.45 (m,2, $CH_2$), 4.28 (s,1, CH), 7.45 (s,4, Ar), 8.44 (s,1, NH); (CI, $CH_4$) MS: m/z=348(M+1). Analysis for $C_{20}H_{20}F_3NO$: Calculated C, 69.15; H, 5.80; N, 4.03; Found: C, 69.01; H, 5.83; N, 3.98.

The title compound was resolved into its two enantiomers by high pressure liquid chromatography, using a 250 mm×20 mm column packed with a silica-based column packing with an ovomucoid stationary phase (Ultron ES-OVM) and eluting with 30% acetonitrile: 70% 0.013M $KH_2PO_4$ (adjusted to pH 5 with 1.0M KOH) at a flow rate of 15.6 ml/min. The enantiomers were detected by spectrophotometer at a wavelength of 250 nm.

The necessary acridinedione starting material may be prepared as follows:

A stirred mixture of 3-trifluoromethylbenzaldehyde (3.48 g), 1,3-cyclohexanedione (4.49 g), ammonium acetate (2.31 g) and ethanol (40 ml) was refluxed for 18 hours. The mixture was cooled and the yellow needles were collected, washed with water and dried in vacuo to give the title compound (6.38 g); mp>300 C; NMR: 1.7–2.0 (m,4), 2.19–2.25 (m,4), 2.50–2.56 (m,4), 4.98 (s,1), 7.41 (s,3), 7.48 (s,1), 9.48 (s,1); MS: m/z=362(M+1). Found for $C_{20}H_{18}F_3NO_2$: C., 66.44; H, 5.00; N, 3.80.

EXAMPLE 29

9-(3-Fluorophenyl)-3,4,5,6,7,8,9,10-octahydro-1(2H)-acridinone.

A mixture of 9-(3-fluorophenyl)-3,4,6,7,9,10-hexahydro-1,8(2H,5H)-acridinedione (5.0 g), sodium borohydride (6.1 g), ethanol (140 mL) and pyridine (50 mL) was heated at 70° C. overnight and cooled to room temperature. The solvent was removed and the resulting yellow solid was collected and washed well with water. Chromatography (ethyl acetate/hexane; 80/20) provided the title compound (2.1 g) as a yellow solid. Recrystallization from ethanol/hexane returned analytically pure light yellow solid, mp 249°–251° C.; NMR: 1.45–1.55 (m,3, $CH_2$), 1.66–1.90 (m,5, $CH_2$); 2.10–2.15 (m,4, $CH_2$), 2.39–2.45 (m,2, $CH_2$), 4.19 (s,1, CH), 6.87–6.92 (m,2, Ar), 7.00 (d,1, J=7.8, Ar), 7.20–7.27 (m,1, Ar), 8.41 (s,1, NH); (CI, $CH_4$) MS: m/z=298(M+1). Analysis for $C_{19}H_{20}FNO$: Calculated C, 76.74; H, 6.78; N, 4.71; Found: C, 76.32; H, 6.71; N, 4.62.

The necessary acridinedione starting material may be prepared according to the method of Example 28 but using 3-fluorobenzaldehyde instead of 3-trifluoromethylbenzaldehyde. M.p.>350° C. Found for $C_{19}H_{18}NFO_2$: C., 73.30, H,5.87; N,4.37.

EXAMPLE 30

9-Phenyl-3,4,5,6,7,8,9,10-octahydro-1(2H)-acridinone.

A mixture of 9-phenyl-3,4,6,7,9,10-hexahydro-1,8(2H,5H)-acridinedione (5.0 g), sodium borohydride (6.5 g), ethanol (150 mL) and pyridine (50 mL) was heated at 70° C. overnight and cooled to room temperature. The solvent was removed, the residue partitioned between water and ethyl acetate, the organic layer was dried and the solvent removed. Chromatography (methylene chloride/methanol; 98/2) provided the title compound (3.0 g) as a white solid. Recrystallization from ethanol/hexane returned analytically pure title compound, mp 252°–254° C., NMR: 1.41–1.51 (m,3, $CH_2$), 1.60–1.88 (m,5, $CH_2$), 2.03–2.13 (m,4, $CH_2$), 2.38–2.44 (m,2, $CH_2$), 4.14 (s,1, CH), 7.04–7.21 (m,5, Ar) 8.34 (s,1, NH); (CI, $CH_4$) MS: m/z=280(M+1). Analysis for $C_{19}H_{21}NO \cdot 0.2H_2O$: Calculated C, 80.64; H, 7.62; N, 4.95; Found: C, 80.84; H, 7.62; N, 4.80.

The necessary acridinedione starting material may be prepared according to the method described in Example 28, but using benzaldehyde instead of 3-trifluoromethylbenzaldehyde.

EXAMPLE 31

9-(3-Bromophenyl)-3,4,5,6,7,8,9,10-octahydro-1(2H)-acridinone.

To a stirred 70° C. mixture of 9-(3-bromophenyl)-3,4,6,7,9,10-hexahydro-1,8(2H,5 H)-acridinedione (5.0 g, 13.4), ethanol (120 mL) and pyridine (40 mL) was added sodium borohydride (7.5 g) in three portions over six hours. The solvent was removed; the resulting yellow solid washed well with water and air dried to provide the title compound (4.8 g). Recrystallization from ethanol/hexane returned analytically pure yellow solid, mp 258°–260° C.; NMR: 1.41–1.51 (m,3, $CH_2$), 1.60–1.88 (m,5, $CH_2$), 2.09–2.15 (m,4, $CH_2$), 2.39–2.45 (m,2, $CH_2$), 4.17 (s,1, CH), 7.16–7.21 (m,2, Ar), 7.26–7.29 (m,2, Ar), 8.44 (s,1, NH); (CI, $CH_4$) MS: m/z=360(M+1). Analysis for $C_{19}H_{20}BrNO$: Calculated C, 63.69; H, 5.59; N, 3.91; Found: C, 63.73; H, 5.69; N, 3.94.

The necessary acridinedione starting material may be prepared as described in Example 28, but using 3-bromobenzaldehyde instead of 3-trifluoromethylbenzaldehyde. M.p. 336°–339° C. Found for $C_{19}H_{18}BrNO_2$: C.,61.12; H 4.94; N, 3.64.

EXAMPLE 32

9-(3-Chlorophenyl)-3,4,5,6,7,8,9,10-octahydro-1(2H)-acridinone.

To a stirred 70° C. mixture of 9-(3-chlorophenyl)-3,4,6,7,9,10-hexahydro-1,8(2H, 5H)-acridinedione (5.0 g), ethanol (120 mL) and pyridine (40 mL) was added sodium borohydride (7.5 g) in two portions over six hours. The solvent was removed; the resulting yellow solid washed well with water and dried in vacuo to provide the title compound (5.0 g) as a yellow solid. Recrystallization from ethanol returned analytically pure material, mp 249°–250° C.; NMR: 1.41–1.51 (m,3, $CH_2$), 1.60–1.88 (m,5, $CH_2$), 2.09–2.15 (m,4, $CH_2$), 2.39–2.45 (m,2, $CH_2$), 4.17 (s,1, CH), 7.09–7.15 (m,3, Ar), 7.21–7.26 (m,1, Ar), 8.43 (s,1, NH). (CI, $CH_4$) MS: m/z=314(M+1). Analysis for $C_{19}H_{20}ClNO$: Calculated C, 72.72; H, 6.37; N, 4.46; Found: C, 72.55; H, 6.48; N, 4.49.

The necessary acridinedione starting material may be prepared as described in Example 28, but using 3-chlorobenzaldehyde instead of 3-trifluoromethylbenzaldehyde. M.p.>300° C. Found for $C_{19}H_{18}ClNO_2$: C.,69.34; H,5.57; N, 4.22.

EXAMPLE 33

9-(4-Chlorophenyl)-3,4,5,6,7,8,9,10-octahydro-1(2H)-acridinone.

To a stirred 70° C. mixture of 9-(4-chlorophenyl)-3,4,6,7,9,10-hexahydro-1,8(2H, 5H)-acridinedione (6.0 g), ethanol (160 mL) and pyridine (50 mL) was added sodium borohydride (7.5 g, 198.4 mmole) in two portions over six hours. The solvent was removed; the resulting yellow solid washed well with water and dried in vacuo. Chromatography (methylene chloride/ethyl acetate; 85/15) and recrystallization from ethanol provided the title compound (1.0 g) as a white solid, mp 253°–254° C.; NMR: 1.41–1.51 (m,3, $CH_2$), 1.60–1.88 (m,5, $CH_2$), 2.07–2.14 (m,4, $CH_2$), 2.38–2.41 (m,2, $CH_2$), 4.16 (s,1, CH), 7.16 (d,2, J=8.4, Ar), 7.25 (d,2, J=8.4, Ar), 8.39 (s,1, NH); (CI, $CH_4$) MS: m/z=314(M+1). Analysis for $C_{19}H_{20}ClNO$: Calculated C, 72.72; H, 6.37; N, 4.46; Found: C, 72.35; H, 6.60; N, 4.29.

The necessary acridinedione starting material may be prepared as described in Example 28, but using 4-chlorobenzaldehyde instead of 3-trifluoromethylbenzaldehyde. M.p.>300° C., Found for $C_{19}H_{18}N_2O_5 \cdot 0.5H_2O$; C.,62.74; H,5.26; N,7.53.

EXAMPLE 34

9-(3-Bromo-4-fluorophenyl)-3,4,5,6,7,8,9,10-octahydro-1(2H)-acridinone.

A mixture of 9-(3-bromo-4-fluorophenyl)-3,4,6,7,9,10-hexahydro-1,8(2H,5H)-acridinedione (1.8 g), sodium borohydride (1.74 g), ethanol (40 mL) and pyridine (14 mL) was heated at 70° C. for three and one half hours. The solvent was removed, the residue partitioned between water and ethyl acetate, the organic layer dried and the solvent removed. Chromatography (methylene chloride/ethyl acetate; 7/3) gave the title compound (1.1 g), as a yellow solid, mp 254°–257° C.; NMR: 1.41–1.51 (m,3, $CH_2$), 1.60–1.88 (m,5, $CH_2$), 2.03–2.13 (m,4, $CH_2$), 2.38–2.44 (m,2, $CH_2$), 4.18 (s,1, CH), 7.13–7.24 (m,2, Ar), 7.38 (dd,1, J=6.9, 2.0, Ar), 8.45 (s,1, NH); (CI, $CH_4$) MS: m/z=378(M+1). Analysis for $C_{19}H_{19}FBr$: Calculated C, 60.65; H, 5.09; N, 3.72; Found: C, 60.68; H, 5.09; N, 3.65.

The necessary acridinedione starting material may be prepared as described in Example 28, but using 3-bromo-4-fluorobenzaldehyde in place of 3-trifluoromethylbenzaldehyde. M.p. 308°–310° C. Found for $C_{19}H_{17}BrFNO_2$: C.,58.31; H,4.42; N,3.58.

EXAMPLE 35

4-(3-Bromophenyl)-2-methyl-4,6,7,8-tetrahydro-5(1H)-quinolone.

A mixture of 3-bromobenzaldehyde (2.0 g), 1,3-cyclohexanedione (1.27 g) and ethanol (30 mL) was heated at reflux for three hours. Acetone (0.75 g), ammonium acetate (1.25 g) and a solution of pyrrolidine acetate (1.89 g) in 4 mL of ethanol was added and refluxing continued overnight. The mixture was cooled, filtered and the filtrate concentrated in vacuo. Chromatography (eluant: methylene chloride/methanol; 98/2) and trituration with ethyl ether provided the title compound (0.28 g) as a yellow solid, mp 187°–191° C.; NMR: 1.73 (s,3, $CH_3$), 1.80–1.90 (m,2, $CH_2$), 2.10–2.18 (m,2, $CH_2$), 2.40–2.45 (m,2, $CH_2$), 4.39 (d,1, J=4.7, CH), 4.59 (d,1, J=4.7, CH), 7.12–7.28 (m,4, Ar), 8.50 (s,1, NH; (CI, $CH_4$) MS: m/z=320(M+1). Analysis for $C_{16}H_{16}BrNO$: Calculated C, 60.39; H, 5.07; N, 4.40; Found: C, 60.19; H, 5.27; N, 4.10.

EXAMPLE 36

4-(3-Trifluoromethoxyphenyl)-2-methyl-4,6,7,8-tetrahydro-5(1H)-quinolone.

A solution of 3-(trifluoromethoxy)benzaldehyde (10.00 g) and 1,3-cyclohexanedione (5.90 g) in ethanol (50 mL) was stirred at reflux for 3 hours. Ammonium acetate (6.09 g) and acetone (3.67 g) were added to the cooled mixture, followed by a solution of acetic acid (3.79 g) and pyrrolidine (4.49 g) in ethanol (15 mL). The mixture was stirred at reflux overnight, poured into water and extracted with ethyl acetate (2×200 mL). The combined organics were dried and concentrated to an oil which was purified by chromatography (0–40% v/v ethyl acetate in methylene chloride) to yield the title compound (2.36 g) as an off-white solid, mp 144°–146° C.; NMR: 1.74 (s,3, $CH_3$), 1.78–1.92 (m,2, $CH_2$), 2.14–2.19 (m,2, $CH_2$) 2.42–2.47 (m,2, $CH_2$) (d,1, J=4.8, CH) 4.63 (d,1, J=4.9, CH) 7.01–7.05 (m,2, Ar) 7.17 (d,1, J=7.7, Ar) 7.36 (dd,1, J=7.7, 3.2, Ar), 8.52 (s,1, NH); (CI, $CH_4$) MS: m/z=324(M+1). Analysis for $C_{17}H_{16}NO_2F_3$: Calculated C, 63.15; H, 4.99; N, 4.33; Found: C, 62.88; H, 5.05; N, 4.33.

EXAMPLE 37

4-(3-Fluorophenyl)-2-methyl-4,6,7,8-tetrahydro-5(1H)-quinolone.

A mixture of 3-fluorobenzaldehyde (7.0 g), 1,3-cyclohexanedione (6.61 g) and ethanol (150 mL) was heated at 70° C. overnight and then cooled to room temperature. Acetone (3.93 g), ammonium acetate (6.52 g) and a solution of pyrrolidine acetate (9.83 g) in ethanol (10 mL) was added and heated at 70° C. for three hours and then cooled to room temperature. The solvent was removed and the residue was partitioned between water and ethyl acetate. The organic layer was dried, filtered, and concentrated in vacuo to obtain an amber oil. Chromatography (methylene chloride/ethyl acetate; 9.0/1.0) and recrystallization from ethanol provided the title compound (0.12 g) as a white solid, mp 216°–218° C.; NMR: 1.73 (s,3, $CH_3$), 1.78–1.90 (m,2, $CH_2$), 2.14–2.19 (m,2, $CH_2$), 2.41–2.46 (m,2, $CH_2$), 4.42 (d,1, J=4.8 CH), 4.61 (d,1, J=4.8, CH) 6.86–7.00 (m,3, Ar), 7.25 (m,1, Ar), 8.49 (s,1, NH); (CI, $CH_4$) MS: m/z=258(M+1). Analysis for $C_{16}H_{16}FNO$: Calculated C, 74.69; H, 6.27; N, 5.44; Found: C, 74.39; H, 6.30; N, 5.35.

EXAMPLE 38

3-Cyano-2-methyl-4-(3-nitrophenyl)-4, 6,7,8-tetrahydro-5(1H)quinolone.

3-Aminocrotonitrile (0.91 g), 1,3-cyclohexanedione (1.25 g), and 3-nitrobenzaldehyde (1.70 g) were combined in ethanol (100 mL) and heated at reflux for 7 hours. Removal of solvent and chromatography (ethyl acetate) gave the title compound (2.40 g) as a yellow solid; mp 214°–216° C. NMR: 1.73–2.00 (m,2, $CH_2$), 2.08 (s,3, $CH_3$), 2.13–2.31 (m,2, $CH_2$), 2.41–2.63 (m,2, $CH_2$), 4.66 (s,1, CH), 7.61 (m,1, Ar), 7.68 (dd,1, J=7.7, 1.1 Ar), 7.98 (s,1, Ar), 8.07 (m,1, Ar), 9.66 (s,1, NH); MS: m/z=309(M). Analysis for $C_{17}H_{15}N_3O_3$: Calculated C, 66.01; H, 4.89; N, 13.58; Found: C, 65.78; H, 4.99; N, 13.45.

EXAMPLE 39

2-Trifluoromethyl-4-(3-cyanophenyl)-4,6,7,8-tetrahydro-5(1H)-quinolone.

A suspension of 3-carboxy-2-trifluoromethyl-2-hydroxy-4-(3-cyanophenyl)- 4,6,7,8-tetrahydro- 5(1H)-quinolone (2.25 g) in toluene (100 ml) was treated with p-toluene sulfonic acid monohydrate (0.33 g). The mixture was vigorously refluxed under Dean-Stark conditions for 1.5 hours and then partitioned between water and ethyl acetate. The organic portion was washed (water and brine) and evaporated. The residue was purified by chromatography (hexane/ethyl acetate, 1:1) to yield the title compound (1.04 g) as a white solid; m.p. 182°–183° C.; NMR: 1.80–2.00(m,2, $CH_2$), 2.13–2.30(m,2,$CH_2$), 2.50–2.67(m,2,$CH_2$), 4.68(d,1, CH, J=5.2), 5.61(d,1, CH, J=5.3), 7.51(m,2, Ar), 7.60(s, 1, Ar), 7.64(m,1, Ar), 9.42(s, 1, NH); MS: m/z=318(M); Analysis for $C_{17}H_{13}F_3N_2O$: Calculated C, 64.15; H, 4.12; N, 8.80; Found: C, 64.15; H, 4.10; N, 8.63.

The starting 3-carboxy-2-trifluoromethyl-2-hydroxy-4-(3-cyanophenyl)-4,6,7,8-tetrahydro- 5(1H)-quinolone was prepared as follows:

A mixture of ethyl 4,4,4-trifluoroacetoacetate (5.0 ml), 1,3-cyclohexanedione (3.87 g), 3-cyanobenzaldehyde (4.61 g), and ammonium acetate (5.63 g) in ethanol (250 ml) was refluxed for 5 hours. The resulting precipitate was collected by filtration (3.39 g). The filtrate was concentrated and purified by chromatography (hexane/ethyl acetate) to provide additional product (5.77 g). The 3-carboethoxy-2-trifluoromethyl-2-hydroxy-4-(3-cyanophenyl)-4,6,7,8-tetrahydro-5( 1H)-quinolone product was obtained as a white solid; MS: m/z=408(M); NMR: 0.86(t,3,$CH_3$, J=7.0), 1.08–1.97(m,2,$CH_2$), 2.00–2.13(m,2,$CH_2$), 2.27–2.40(m,1, $CH_2$), 2.53–2.67(m,1,$CH_2$), 2.74(d,1,CH, J=12.2), 3.77–3.80(m,2,$CH_2$), 3.98(d,1,CH, J=11.7), 7.24(s,1,OH), 7.33–7.47(m,2,Ar), 7.50(s,1,Ar), 7.59(m,1,Ar) 8.10(s,1, NH).

A suspension of 3-carboethoxy-2-trifluoromethyl-2-hydroxy-4-(3-cyanophenyl)-4,6,7,8-tetrahydro- 5(1H )-quinolone (3.39 g) in ethanol (20 ml) and water (20 ml) was treated with lithium hydroxide monohydrate (0.75 g). The mixture was heated at 90° C. for 1.5 hours, diluted with water, acidified with 1N hydrochloric acid, and extracted with ethyl acetate. The combined organic extracts were washed (water and brine), dried, filtered, and evaporated to yield a foam which was purified by chromatography (ethyl acetate and ethyl acetate/methanol, 3:1) to afford 3-carboxy-2-trifluoromethyl-2-hydroxy-4-(3-cyanophenyl)- 4,6,7,8-tetrahydro-5(1H)-quinolone (2.67 g ) as a pale yellow foam; MS: m/z=381(m).

EXAMPLE 40

2-Methyl-4-(3-chloro-4-fluorophenyl)-4,6,7,8-tetrahydro-5(1H)-quinolone.

A mixture of 3-chloro-4-fluoro benzaldehyde (2.7 g), 1,3-cyclohexanedione (1.99 g) and 47 mL of ethanol were heated at 50° C. overnight and then cooled to room temperature. Acetone (1.18 g), ammonium acetate (1.97 g) and a premixed solution of pyrrolidine acetate (20.4 mmole) in 5 mL of ethanol were added and heated at 70° C. for three hours and then cooled to room temperature. The solvent was evaporated in vacuo and the residue was partitioned between water and ethyl acetate. The organic layer was dried over magnesium sulfate, filtered, and concentrated in vacuo. Chromatography (eluant: ether/hexane; 9.0/1.0) over silica gel provided the title compound 0.140 g as a yellow solid, m.p. 164°–167° C. 1H-NMR (300 MHz, d6-DMSO): 1.74(s, 3H,$CH_3$), 1.81–1.88(m, 2H, $CH_2$) 2.15–2.19(m,2H, $CH_2$), 2.41–2.48(m,2H,CH2), 4.41(d,1H, J=4.8 Hz, CH), 4.60(d, 1H, J=4.8(Hz,CH), 7.10–7.28(m,3H, aromatic), 8.54(s, 1H, NH); MS (CI, CH4): 292 (M+1): Analysis for $C_{16}H_{15}ClFNO$: Calculated: C; 65.87; H; 5.18; N; 4.80: Found: C; 65.67; H; 5.50; N; 4.48.

EXAMPLE 41

9-(3-Trifluoromethyl-4-cyanophenyl)-3,4,5,6,7,8,9,10-octahydro-1-(2H)-acridinone.

A mixture of 9-(3-trifluoro-4-cyanomethylphenyl)-3,4,6,7,9,10-hexahydro-1,8-(2H,5H)-acridinedione (0.75 g) and sodium borohydride (0.73 g) and 17 mL of ethanol and 6 mL of pyridine were heated at 70° C. for 3 hours and then cooled at room temperature. The solvent was removed in vacuo and the residue was partitioned between water and ethyl acetate. The organic layer was dried over magnesium sulfate, filtered and concentrated in vacuo. Chromatography (eluant: methylene chloride/ethyl acetate; 9.0/1.0 and trituration from ether/hexane provided the title compound (11 g) as a yellow solid; m.p. 210°–212° C.; 1H-NMR (300 MHz, d6-DMSO): 1.47–1.89(m,8H,CH2), 2.05–2.16(m,4H,CH2), 2.40–2.45(m,2H,CH2), 4.41(s,1H,CH), 7.63(d,1H, J= 8.0 Hz, aromatic), 7.74(s,1H, aromatic) 8.04(d,1H, J=8.0 Hz, aromatic) 8.59(s, 1H, NH); MS(CI, $CH_4$): 373(M+1); Analysis for $C_{21}H_{19}F_3N_2O$, Calculated: C; 67.73; H; 5.14; N; 7.52; Found: C, 67.76; H; 5.31; N; 7.46.

The necessary acridineodione starting material may be prepared as described in Example 28, but using 4-cyano-3-trifluoromethylbenzaldehyde; m.p. 289°–291° C., Found $C_{21}H_{17}F_3N_2O_2$: C., 65.08; H, 4.40; N, 7.22.

EXAMPLE 42

9-(3-Chloro-4-fluoro)-3,4,5,6,7,8,9,10-octahydro-1-(2H)-acridinone.

A mixture of 9-(3-chloro-4-fluoro)-3,4,6,7,9,10-hexahydro-1,8-(2H,5H)-acridinedione (1.5 g) and sodium borohydride (1.64 g) and 38 mL of ethanol and 13 mL of pyridine were heated at 70° C. for 3.5 hours and then cooled to room temperature. The solvent was removed in vacuo and the residue was partitioned between water and ethyl acetate. The organic layer was dried over magnesium sulfate, filtered, and concentrated in vacuo. Chromatography (eluent: methylene chloride/ethyl acetate; 8.0/2.0) over silica gel provided the title compound (0.75 g) as a yellow solid, m.p. 236°–239° C. 1H-NMR (300 MHz, d6-DMSO): 1.41–1.51(m,3H, CH2) 1.60–1.88(m,5H,CH$_2$), 2.09–2.15(m,4H CH2) 2.38–2.44(m,2H, CH2), 4.19(s,1H, CH), 7.10–7.16(m,1H, aromatic), 7.21–7.27(m,2H, aromatic) 8.45 (s,1H,NH), MS(CI, CH$_4$): 332(M+1); Analysis for $C_{19}H_{19}FClNO$. 0.1H$_2$O. Calculated: C; 68.40; H; 5.80; N; 4.20. Found: C; 68.30; H; 5.84; N; 4.05.

The necessary acridineolione starting material may be prepared as described in Example 28, but using 3-chloro-4-fluorobenzaldehyde; m.p. 325°–328° C.; Found for $C_{19}H_{17}ClFNO_2$: C., 65.78; H, 4.88; N, 3.98.

EXAMPLE 43

(–)-4-(3-Cyanophenyl)-2-trifluoromethyl-4,6,7,8-tetrahydro-5(1H)-quinolone.

A stirred solution of (–)-4-(3-cyanophenyl)-2-trifluoromethyl-5-oxo-1,4,5,6,7,8-hexahydroquinoline- 3-carboxylic acid (3.93 g, 10.85 mmol) in N-methylpyrrolidin-2-one (24 mL) was placed in a preheated oil bath at 210° C. for 20 minutes. The cooled reaction mixture was then poured into water (200 mL) and extracted twice with ethyl ether. The combined ether extracts were washed twice with water, dried (MgSO$_4$), filtered and the solvent removed to yield an off-white solid. Chromatography (eluent: methylene chloride/ether 9:1) and trituration with ethyl ether/hexane provided the title compound (3.42 g, 79%) as a white solid mp 187°–189° C. NMR: 1.88–1.91 (m, 2H, CH$_2$), 2.21–2.25 (m, 2H, CH$_2$), 2.53–2.64 (m, 2H, CH$_2$), 4.68(d, 1H, J=5.3 Hz, CH), 5.61 (d, 1H, J=5.3 Hz, CH), 7.50–7.54 (m, 2H, Ar), 7.61–7.66 (m, 2H, Ar), 9.42 (s, 1H, NH); MS: m/z=319(M+1); $[\alpha]_D^{23}$=–606.8° (c=0.665, methanol). Analysis for $C_{17}H_{13}F_3N_2O$: Calculated C, 64.14; H, 4.12; N, 8.80; Found: C, 64.07; H, 4.24; N, 8.78.

$^{19}$F-NMR analysis of this material in the presence of the chiral shift reagent (R)-(–)-1-(9-anthryl)-2,2,2-trifluoroethanol-d$_{11}$ CDCl$_3$ at –30° C.) showed the (–)-enantiomer to be present in approximately 99% ee.

The intermediate (–)-4-(3-cyanophenyl)-2-trifluoromethyl-5-oxo-1,4,5,6,7,8-hexahydroquinoline- 3-carboxylic acid was prepared as follows.

a. (±)-Isobornyl 4,4,4-trifluoroacetoacetate. A stirred mixture of ethyl 4,4,4-trifluoroacetoacetate (160.28 g 870 mmol) and (±)-isoborneol (86.81 g 563 mmol) was stirred at 130° C. (bath temperature) for 18 hours under a 4 inch Vigreaux column which allowed ethanol to distill off. The bath temperature was then increased to 150° C. to distill the residual ethanol; a total of 29 mL (88% of theory) was collected. The remaining mixture was then fractionated at reduced pressure to yield (±)-isobornyl 4,4,4-trifluoroacetoacetate as a colorless oil (124.6 g 76%); bp 84°–92°/0.4 torr; NMR CDCl$_3$): 0.82–1.17 (m, 11H, CH$_3$, CH$_2$) 1.55–1.84 (m, 5H, CH$_2$, CH) 3.72 (s, diketo form CH$_2$) 4.74–4.81 (m, 1H, —OCH) 5.59 (s, enol form CH) 11.97 (s, enol form OH).

b. (±)-Isobornyl 4-(3-cyanophenyl)-2-trifluoromethyl-2-hydroxy-5-oxo- 1,2,3,4,5,6,7,8-octahydroquinoline-3-carboxylate. A stirred mixture of (±)-isobornyl 4,4,4-trifluoroacetoacetate (82.6 g 282.8 mmol), 1,3-cyclohexanedione (31.7 g 282.8 mmol), 3-cyanobenzaldehyde (37.1 g 282.8 mmol), and ammonium acetate (54.4 g 706.3 mmol) in ethanol (2070 mL) was refluxed for 4 hours. After removal of precipitated 9-(3-cyanophenyl)-3,4,6,7,9,10-hexahydro-1,8-(2H, 5H)-acridinedione by filtration, the filtrate was concentrated in vacuo. Chromatography (eluent: ethyl acetate/hexane 7:3) provided (±)-isobornyl 4-(3-cyanophenyl)-2-trifluoromethyl-2-hydroxy-5-oxo-1,2,3,4,5,6,7,8-octahydroquinoline- 3-carboxylate 92 g (63%) as a white solid; mp 209°–213° C. dec; NMR: 0.63–0.73 (m, 9H, CH$_3$), 0.86–1.64 (m, 7H, CH$_2$, CH), 1.84–1.88 (m, 2H, CH$_2$), 2.03–2.07 (m, 2H, CH$_2$), 2.34–2.63 (m, 2H, CH$_2$) 2.64–2.72 (m, 1H, CH), 3.92–3.96 (d, 1H, CH), 4.10–4.16 (m, 1H, CH), 7.22–7.25 (d, 1H, OH), 7.39–7.45 (m, 2H, Ar), 7.49 (s, 1H, Ar), 7.57–7.61 (m, 1H, Ar), 8.11–8.13 (d, 1H, Ar); MS: m/z=517(M+1). Analysis for $C_{28}H_{31}F_3N_2O_4$: Calculated: C; 65.10; H; 6.05; N; 5.42; Found: C; 64.93; H; 6.05; N; 5.22.

c. 4-(3-Cyanophenyl)-2-trifluoromethyl-5-oxo-1,4,5,6,7, 8-hexahydroquinoline-3-carboxylic acid. A stirred mixture of (±)-isobornyl 4-(3-cyanophenyl)-2-trifluoromethyl-2-hydroxy-5-oxo-1,2,3,4,5,6,7,8-octahydroquinoline- 3-carboxylate (8.5 g 16.5 mmol), p-toluenesulfonic acid (1.05 g 5.5 mmol) and toluene (170 mL) was refluxed for 3 hours. The reaction mixture consisted of an insoluble gum which contained the desired acid and toluene solution. To prevent decarboxylation, only enough heat was applied to the reaction mixture to obtain a mild reflux. After removal of solvent, the residue was partitioned between ethyl acetate and water. The ethyl acetate was washed with water, separated and extracted twice with saturated aqueous sodium bicarbonate. The stirred combined sodium bicarbonate extracts were cooled in an ice bath and concentrated hydrochloric acid was added dropwise until the solution was strongly acidic. The mixture was extracted with ether and the ether layer was dried, filtered, and concentrated in vacuo to give a yellow oily gum. Trituration with methylene chloride/hexane yielded the carboxylic acid (1.8 g, 31%) as an off-white solid. The material was identical by NMR and tlc (silica gel-10% methanol in chloroform containing a few drops of acetic acid) to the material described and characterized in sub-part i. of Example 43.

The ethyl acetate layer was dried, and evaporated, to obtain impure (±)-isobornyl 4-(3-cyanophenyl)-2-trifluoromethyl-5-oxo-1,4,5,6,7,8-hexahydroquinoline- 3-carboxylate, which was identical to a previously prepared and characterized sample; white solid; mp 179°–180° C.; NMR: 0.61–0.72(m, 9H, CH$_3$), 1.00–2.6 (m, 13H, CH$_2$, CH), 4.45–4.57 (m, 1H, CH), 4.88–4.92 (d, 1H, CH), 7.46–7.55 (m, 3H, Ar), 7.65–7.69 (m, 1H, Ar), 9.70–9.71 (d, 1H, NH). MS(CI, CH$_4$): 517 (M+1). Analysis for $C_{28}H_{29}F_3N_2O_4$: Calculated: C; 67.46; H; 5.86; N; 5.62; Found: C; 67.29; H; 5.99; N; 5.71.

The recovered (±)-isobornyl 4-(3-cyanophenyl)-2-trifluoromethyl-5-oxo-1,4,5,6,7,8-hexahydroquinoline- 3-carboxylate was subjected to conditions similar to those described in Example 43.c. to yield an additional 1.1 g of 4-(3-cyanophenyl)-2-trifluoromethyl-5-oxo-1,4,5,6,7,8-hexahydroquinoline- 3-carboxylic acid, for a total yield of 2.9 g (49%).

d. S-(−)-α-Methylbenzylamine (−)-4-(3-cyanophenyl)-2-trifluoromethyl-5-oxo- 1,4,5,6,7,8-hexahydroquinoline-3-carboxylic acid salt. To a stirred solution of racemic 2-trifluoromethyl-4-(3-cyanophenyl)-5-oxo-1,4,5,6,7,8-hexahydroquinoline- 3-carboxylic acid (28.2 g, 77.84 mmol) in n-butanol (211 mL) was added toluene (1000 mL) followed by a solution of S-(−)-α-methyl benzylamine (9.4 g, 77.84 mmol) in toluene (198 mL). After standing at ambient temperature overnight overnight, the resulting precipitate was filtered, and washed with toluene and ethyl ether to yield 32 g of a white salt. Five recrystallizations from toluene/n-butanol (3:1) provided the salt as a white solid (7.77 g); mp softens and turns glasslike at 112°–115° C., liquid melt 148°–150° C.; NMR: 1.36–1.38 (d, 3H, $CH_3$), 1.75–1.88 (m, 2H, $CH_2$), 2.19–2.23 (m, 2H, $CH_2$), 2.49–2.61 (m, 2H, $CH_2$), 3.35–3.42 (m, exchangeables, water) 4.24–4.26 (q, 1H, J=6.8 Hz, CH), 4.91 (s, 1H, CH), 7.16–7.60 (m, 9H, Ar); MS: m/z=363(M+1); $[\alpha]_D = -180.5°$ (c=1.075, methanol, 23° C.); 99% ee by $^{19}F$-NMR in $CDCl_3$. Analysis for $C_{26}H_{24}F_3N_3O_3 \cdot 1.0\ C_4H_9OH \cdot 0.5\ H_2O$: Calculated C, 63.59; H, 6.23; N, 7.42; Found: C, 63.66; H, 6.15; N, 7.06.

e. (−)-4-(3-Cyanophenyl)-2-trifluoromethyl-5-oxo-1,4,5,6,7,8-hexahydroquinoline-3-carboxylic acid. To a cooled,(ice bath) stirred slurry of S-(−)-α-methylbenzylamine (−)-4-(3-cyanophenyl)-2-trifluoromethyl-5-oxo- 1,4,5,6,7,8-hexahydroquinoline-3carboxylic acid salt (7.5 g, 15.5 mmol) in water (150 mL) was added concentrated hydrochloric acid dropwise until the mixture was strongly acidic. The mixture was extracted twice with ethyl ether, and the combined ether layer was dried, filtered and the solvent removed to yield a yellow foam. Trituration with dichloromethane returned 4.9 g (88%) of the carboxylic acid as a pale yellow solid; mp 206°–208° C.; NMR: 1.74–1.95 (m, 2H, $CH_2$), 2.18–2.32 (m, 2H, $CH_2$), 2.54–2.73 (m, 2H, $CH_2$), 4.92 (s, 1H, CH), 7.47–7.52 (m, 3H, Ar), 7.64–7.68 (m, 1H, Ar), 9.60 (s, 1H, NH), 13.07(s, 1H, COOH); MS: m/z=363(M+1).

The intermediate 4-(3-cyanophenyl)-2-trifluoromethyl-5-oxo-1,4,5,6,7,8-hexahydroquinoline-3-carboxylic acid described at Example 43.c. can alternatively be prepared as follows.

f. 2-Cyanoethyl hemiacetal of 2-cyanoethyl 4,4,4-trifluoroacetoacetate. A mixture of ethyl 4,4,4-trifluoroacetoacetate (30 mL 205 mmol) and 3-hydroxypropionitrile (7.11 g 100 mmol) was stirred at 150° C. (bath temperature) for 18 hours under a 4 inch Vigreaux column which allowed ethanol to distill off. The remaining mixture was then fractionated at atmospheric pressure. The fraction distilling at 222°–228° C. (11.71 g) was determined to contain approximately 50 mole % of the 2-cyanoethyl hemiacetal of 2-cyanoethyl 4,4,4-trifluoroacetoacetate by NMR and mass spectral analysis; NMR $CDCl_3$): 2.43–2.65 (m, 2H) 2.76–2.99 (m, 4H) 3.78–3.82 (m, 1H) 4.13–4.15 (m, 1H) 4.33–4.57 (m, 2H) 5.96 (s, 1H, OH).

g. 2-Cyanoethyl 4-(3-cyanophenyl)-2-trifluoromethyl-2-hydroxy-5-oxo- 1,2,3,4,5,6,7,8-octahydroquinoline-3-carboxylate. A stirred mixture of the material from Example 43.f. along with 3-cyanobenzaldehyde (7.34 g 56 mmol), 1,3-cyclohexanedione (6.83 g 56 mmol) and ammonium acetate (13.10 g 170 mmol) in ethanol (400 mL) was stirred at reflux for 10 hours. The cooled solution was filtered to remove precipitated 9-(3-cyanophenyl)-3,4,6,7,9,10-hexahydro-1,8-(2H,5H)-acridinedione. The filtrate was evaporated to dryness and the residue chromatographed (eluent methylene chloride, 1:1 ethyl acetate/methylene chloride and ethyl acetate) to yield 4.14 g of 2-cyanoethyl 4-(3-cyanophenyl)-2-tri-fluoromethyl-2-hydroxy-5-oxo- 1,2,3,4,5,6,7,8-octahydroquinoline-3-carboxylate; NMR: 1.86–1.90 (m, 2H, $CH_2$) 1.94–2.18 (m, 2H, $CH_2$) 2.31–2.38 (m, 1H, aliphatic) 2.50–2.72 (m, 3H, aliphatic) 2.82 (d, 1H, aliphatic, J=11.9) 3.35 (br.s, 1H, aliphatic) 3.94–4.02 (m, 2H, aliphatic) 7.37–7.59 (m, 5H, Ar, OH) 8.16 (s, 1H, NH); MS: m/z=434(M+1).

h. 2-Cyanoethyl 4-(3-cyanophenyl)-2-trifluoromethyl-5-oxo-1,4,5,6,7,8-hexahydroquinoline-3-carboxylate. A mixture of 2-cyanoethyl 4-(3-cyanophenyl)-2-trifluoromethyl-2-hydroxy-5-oxo- 1,2,3,4,5,6,7,8-octahydroquinoline-3-carboxylate (4.14 g 9.6 mmol), p-toluenesulfonic acid (0.61 g 3.2 mmol) and toluene (100 mL) was stirred at reflux under a Dean-Stark apparatus for 2 hours. The reaction mixture, which consisted of dark oil and toluene phases, was cooled and poured on a 1.5 inch diameter chromatography column containing 90 g of silica gel. The mixture was washed on the column with a little ethyl acetate. Elution with ethyl ether and trituration of the resulting solid with ethyl ether yielded the ester as a yellow-orange solid (2.84 g, 72%); mp 148°–151.5° C.; NMR: : 1.79–1.99 (m, 2H, $CH_2$) 2.19–2.33 (m, 2H, $CH_2$) 2.50–2.74 (m, 2H, $CH_2$) 2.85 (t, 2H, $CH_2$) 4.15–4.27 (m, 2H, $CH_2$) 4.94 (s, 1H, CH) 7.47–7.63 (m, 3H, Ar) 7.65–7.67 (m, 1H, Ar) 9.84 (s, 1H, NH); MS: m/z=416(M+1). Analysis for $C_{21}H_{16}F_3N_3O_3$: Calculated C, 60.72; H, 3.88; N, 10.12; Found: C, 60.63; H, 3.80; N, 9.89.

i. 4-(3-Cyanophenyl)-2-trifluoromethyl-5-oxo-1,4,5,6,7,8-hexahydroquinoline-3-carboxylic acid. To a cooled (ice bath) stirred slurry of 2-cyanoethyl 2-trifluoromethyl-4-(3-cyanophenyl)-5-oxo-1,4,5,6,7,8-hexahydroquinoline- 3-carboxylate (2.80 g 6.74 mmol) in 1,2-dimethoxyethane (8.5 mL) was added dropwise over a 10 minute period a pre-cooled solution of sodium hydroxide (0.80 g 20.0 mmol) in water (6.5 mL). A dark brown solution was obtained as starting ester dissolved. After stirring at room temperature for 2 hours the yellowish-brown solution was diluted with water (16 mL), returned to the ice bath and stirred as the mixture was treated with concentrated hydrochloric acid (2 mL). A brown oil precipitated which upon stirring solidified to a cream colored solid. The solid was filtered and washed with cold water. The material was dried at 50°/0.1 torr overnight to give the carboxylic acid (2.33 g, 95%); mp 209 211° C. dec. with gas evolution; NMR: 1.75–1.88 (m, 1H, $CH_2$) 1.89–1.95 (m, 1H, $CH_2$) 2.18–2.32 (m, 2H, $CH_2$) 2.54–2.73 (m, 2H, $CH_2$) 4.92 (s, 1H, CH) 7.47–7.54 (m, 3H, Ar) 7.65–7.67 (m, 1H, Ar) 9.62 (s, 1H, NH) 13.10 (s, 1H, $CO_2H$); MS: m/z=363(M+1). Analysis for $C_{18}H_{13}F_3N_2O_3$: Calculated C, 59.67; H, 3.62; N, 7.73; Found: C, 59.53; H, 3.84; N, 7.69.

EXAMPLE 44

The following illustrate representative pharmaceutical dosage forms containing a compound of formula I, for example as illustrated in any of the previous Examples, (hereafter referred to as "compound X"), for therapeutic or prophylactic use in humans:

|  | mg/tablet |
|---|---|
| (a) Tablet |  |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule |  |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

FORMULAE

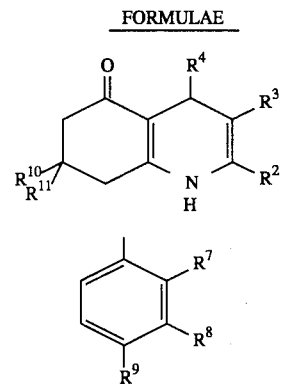
I

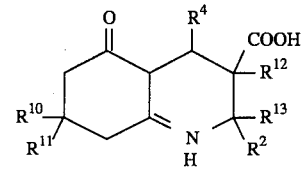
III

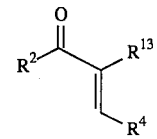
IV

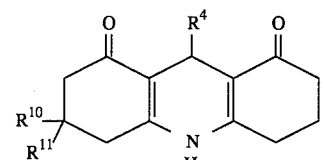
VI

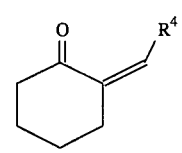
VII

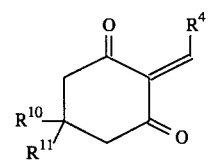
XII

XIII

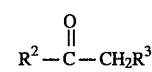
XIV

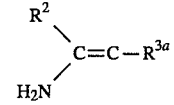
XV

SCHEME I

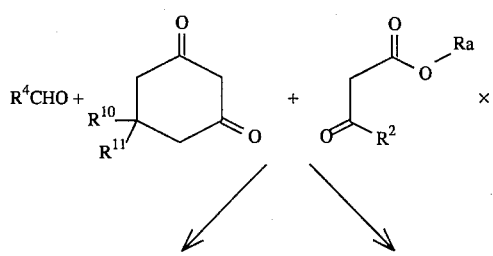

SCHEME I

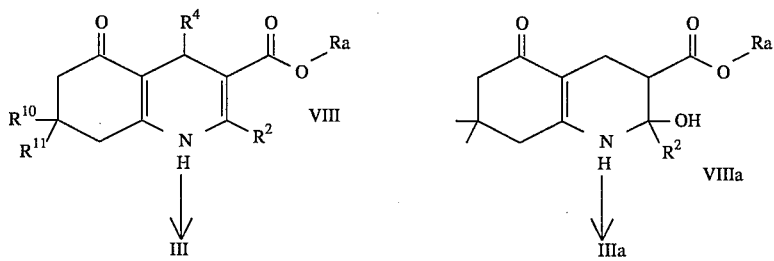

SCHEME II

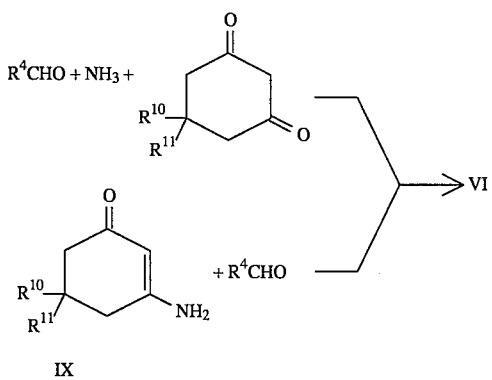

SCHEME III

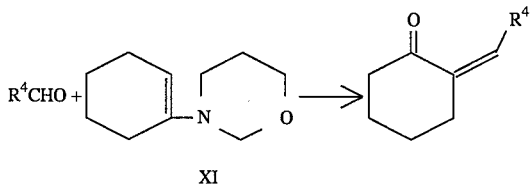

We claim:

1. A compound of Formula I

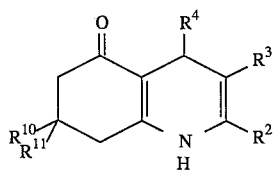

or a pharmaceutically acceptable salt thereof, wherein: either $R^2$ is hydrogen, (1–6C) alkyl or (1–4C)fluoroalkyl; and $R^3$ is hydrogen, cyano, (1–6C)alkyl, (1–6C) fluoroalkyl or ethanoyl; or $R^2$ and $R^3$ when taken together form a 1,4-butandiyl;

$R^4$ is 2- or 3-thienyl or furyl substituted at the 4- and/or 5-position(s) by a radical or radicals independently selected from a group (a) consisting of nitro, cyano, halo, (1–4C)alkyl, (1–4C)alkyl-sulphonyl and 2-thienyl provided that a 3-thienyl or furyl group may only be substituted at the 5-position; or $R^4$ is a 2-pyridyl which is substituted at the 5 position and/or either at the 4 position or the 6 position by a member of the above group (a); or $R^4$ is a 3-pyridyl which is substituted at the 6 position by a member of the above group (a); or $R^4$ is a 4-pyridyl which is a substituted at the 2 position by a member of the above group (a); or $R^4$ is a group of Formula II,

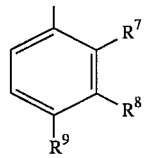

wherein:

$R^7$ is hydrogen; and $R^8$ and $R^9$ are independently selected from hydrogen, hydroxy (1–4C)alkoxy, nitro, cyano, (1–4C) fluoroalkyl, (1–4C)fluoroalkoxy, halo, (1–4C)alkyl, (1–4C)alkanoyl, phenyl and (1–4C)alkylsulphonyl; or $R^8$ and $R^9$ taken together are (1–3C)alkylenedioxy; and $R^{10}$ and $R^{11}$ are each independently hydrogen or (1–4C)alkyl, but excluding 3-cyano-4-phenyl-2,7,7-trimethyl-4,6,7,8-tetrahydro-5(1H) -quinolone a 3-ethanoyl-4-phenyl-2,7,7-trimethyl-4,6,7,8-tetrahydro-5(1H)-quinolone.

2. A compound as claimed in claim 1, in which either $R^2$ is methyl, ethyl, propyl, isopropyl, butyl, isobutyl, sec-butyl, tert-butyl or trifluoromethyl; and $R^3$ is hydrogen, cyano, ethanoyl; or $R^2$ and $R^3$ when taken together form a 1,4-butandiyl.

3. A compound as claimed in claim 2, in which $R^3$ is hydrogen;

or $R^2$ and $R^3$ when taken together form a 1,4-butandiyl.

4. A compound as claimed in claim 3, in which $R^2$ is trifluoromethyl.

5. A compound as claimed in claim 1 or claim 2 in which $R^4$ is 4-bromo-2-thienyl, 5-bromo-2-thienyl, 5-methylsulphonyl-2-thienyl, 5-methyl-2-thienyl, 5-(2-thienyl)-2-thienyl, 4-nitro-2-thienyl, 5-nitro-2-thienyl, 4-cyano-2-thienyl, and 5-nitro-3-thienyl or is a group of formula II in which $R^8$ is selected from hydrogen, hydroxy, methoxy, nitro, cyano, trifluoromethyl, trifluoromethoxy, methyl, ethyl, isopropyl, halo and ethanoyl, and $R^9$ is selected from hydrogen, hydroxy, methoxy, nitro, cyano, trifluoromethyl, trifluoromethoxy, methyl, ethyl, isopropyl and halo.

6. A compound as claimed in claim 5, in which $R^4$ is phenyl, 3-methoxyphenyl, 3-nitrophenyl, 3-cyanophenyl, 3-trifluoromethylphenyl, 3-trifluoromethyl-4-cyanophenyl, 4-trifluoromethylphenyl, 3-trifluoromethoxyphenyl, 3-fluorophenyl, 3-chlorophenyl, 3-chloro-fluorophenyl, 3-bromophenyl, 4-fluorophenyl, 4-chlorophenyl, 3-bromo-4-fluorophenyl, 3,4-dichlorophenyl, 4-methylphenyl, 3,4-methylenedioxyphenyl and 4-nitro-2-thienyl.

7. A compound as claimed in claim 6, in which $R^4$ is 3-nitrophenyl or 3-cyanophenyl.

8. A compound as claimed in claim 1 or claim 2, in which $R^{10}$ and $R^{11}$ are both hydrogen or both methyl.

9. A compound as claimed in claim 1, in which either $R^2$ is methyl, ethyl, propyl, isopropyl, butyl, isobutyl, sec-butyl, tert-butyl or trifluoromethyl; and $R^3$ is hydrogen; or $R^2$ and $R^3$ when taken together form a 1,4-butandiyl;

$R^4$ is 3-nitrophenyl or 3-cyanophenyl; and $R^{10}$ and $R^{11}$ are both hydrogen.

10. A compound as claimed in claim 1, which is selected from 2-trifluoromethyl-4-(3-nitrophenyl)-4,6,7,8-tetrahydro-5(1H)-quinolone and 2-trifluoromethyl-4-(3-cyanophenyl)-4,6,7,8-tetrahydro-5(1H)-quinolone.

11. A compound as claimed in claim 1, which is (–)-4-(3-cyanophenyl)-2-trifluoromethyl-4,6,7,8-tetrahydro-5(1H)-quinolone.

12. A pharmaceutical composition, which comprises, a compound of formula I or a pharmaceutically acceptable salt thereof, as defined in claim 1, and a pharmaceutically acceptable diluent or carrier.

13. A pharmaceutical composition, which comprises, (–)-4-(3-cyanophenyl)-2-trifluoromethyl-4,6,7,8-tetrahydro-5(1H)-quinolone or a pharmaceutically acceptable salt thereof, and a pharmaceutically acceptable diluent or carrier.

14. A method for the treatment of urinary incontinence, comprising administering to a mammel in need of such treatment an effective amount of a compound of formula I or a pharmaceutically acceptable salt thereof as defined in claim 1.

15. A method for the treatment of urinary incontinence as claimed in claim 14, comprising administering to a mammel in need of such treatment an effective amount of (–)-4-(3-cyanophenyl)-2-trifluoromethyl -4,6,7,8-tetrahydro-5( 1H)-quinolone or a pharmaceutically acceptable salt thereof.

16. A method for relaxing bladder smooth muscle comprising, administering to a mammel in need of such treatment an effective amount of a compound of formula I or a pharmaceutically acceptable salt thereof as defined in claim 1.

17. A method for relaxing bladder smooth muscle as claimed in claim 16 comprising administering to a mammel in need of such treatment an effective amount of (–)-4-(3-cyanophenyl)-2-trifluoromethyl-4,6,7,8-tetrahydro-5( 1H)-quinolone or a pharmaceutically acceptable salt thereof.

18. A compound of formula III

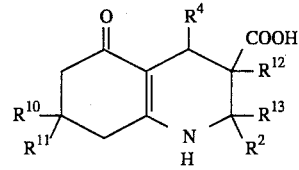

in which either $R^{12}$ and $R^{13}$ together represent a bond or $R^{12}$ is hydrogen and $R^{13}$ is a hydroxy group;

$R^2$ is hydrogen, (1–6C)alkyl or (1–4C)fluoroalkyl; and $R^4$ is 2- or 3-thienyl or furyl substituted at the 4- and/or 5-position(s) by a radical or radicals independently selected from a group (a) consisting of nitro, cyano, halo, (1–4C)alkyl, (1–4C)alkyl-sulphonyl and 2-thienyl provided that a 3-thienyl or furyl group may only be substituted at the 5-position; or $R^4$ is a 2-pyridyl which is substituted at the 5 position and/or either at the 4 position or the 6 position by a member of the above group (a); or $R^4$ is a 3-pyridyl which is substituted at the 6 position by a member of the above group (a); or $R^4$ is a 4-pyridyl which is a substituted at the 2 position by a member of the above group (a); or $R^4$ is a group of Formula II,

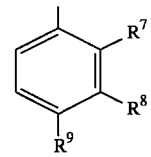

wherein:

$R^7$ is hydrogen; and $R^8$ and $R^9$ are independently selected from hydrogen, hydroxy (1–4C) alkoxy, nitro, cyano, (1–4C)fluoroalkyl, (1–4C)fluoroalkoxy, halo, (1–4C)alkyl, (1–4C)alkanoyl, phenyl and (1–4C)alkylsulphonyl; or $R^8$ and $R^9$ taken together are (1–3C)alkylenedioxy; and $R^{10}$ and $R^{11}$ ar each independently hydrogen or (1–4C)alkyl, but excluding 3-cyano-4-phenyl-2,7,7-trimethyl4,6,7,8-tetrahydro-5(1H)-quinolone and 3-ethanoyl-4-phenyl -2,7,7-trimethyl-4,6,7,8-tetrahydro-5(1H)-quinolone.

19. A compound as claimed in claim 18, which is selected from (–)-4-(3-cyanophenyl)-2-trifluoromethyl-5-oxo-1,4,5,6,7,8-hexahydroquinoline-3-carboxylic acid and 4-(3-cyanophenyl)-2-trifluoromethyl-2-hydroxy-5-oxo-1,2,3,4,5,6,7,8-octahydroquinoline- 3-carboxylic acid.

* * * * *